(12) United States Patent
Cheema et al.

(10) Patent No.: US 11,534,301 B2
(45) Date of Patent: Dec. 27, 2022

(54) APPARATUS AND SYSTEM FOR CHANGING MITRAL VALVE ANNULUS GEOMETRY

(71) Applicants: Asim Cheema, Mississauga (CA); Farrokh Janabi-Sharifi, North York (CA); Ata Taghipour, Toronto (CA)

(72) Inventors: Asim Cheema, Mississauga (CA); Farrokh Janabi-Sharifi, North York (CA); Ata Taghipour, Toronto (CA)

(73) Assignees: Asim Cheema, Mississauga (CA); Farrokh Janabi-Sharifi, North York (CA); Ata Taghipour, Toronto (CA)

( * ) Notice: Subject to any disclaimer, the term of this patent is extended or adjusted under 35 U.S.C. 154(b) by 0 days.

(21) Appl. No.: 16/646,610

(22) PCT Filed: Sep. 11, 2018

(86) PCT No.: PCT/CA2018/051116
§ 371 (c)(1),
(2) Date: Mar. 12, 2020

(87) PCT Pub. No.: WO2019/051587
PCT Pub. Date: Mar. 21, 2019

(65) Prior Publication Data
US 2020/0268511 A1    Aug. 27, 2020

Related U.S. Application Data

(60) Provisional application No. 62/557,349, filed on Sep. 12, 2017.

(51) Int. Cl.
*A61F 2/24* (2006.01)
(52) U.S. Cl.
CPC .......... *A61F 2/2451* (2013.01); *A61F 2/2466* (2013.01)

(58) Field of Classification Search
CPC ........ A61F 2/2442–2448; A61F 2/2451–2457; A61F 2/246; A61F 2/2463–2469
See application file for complete search history.

(56) References Cited

U.S. PATENT DOCUMENTS 6,269,819 B1    8/2001  Oz et al.
6,461,366 B1    10/2002 Seguin
(Continued)

FOREIGN PATENT DOCUMENTS

WO    2004/084746 A2    10/2004
WO    WO-2004084746 A2 * 10/2004 ........... A61F 2/2451

OTHER PUBLICATIONS

International Search Report and Written Opinion dated Dec. 21, 2018 in corresponding International Patent Application No. PCT/CA2018/051116 (11 pages).
(Continued)

*Primary Examiner* — Brian A Dukert
*Assistant Examiner* — Rebecca Lynee Zimmerman
(74) *Attorney, Agent, or Firm* — Bereskin & Parr LLP

(57) ABSTRACT

Examples of an apparatus, system and method for changing a geometry of a mitral valve of a heart are described herein. In one example embodiment, the apparatus comprises an anchor having a body for positioning and anchoring within a coronary sinus vein of the heart. The body has a first end and a second end that is spaced apart from the first end; a longitudinally extending axis; and a wall with an interior volume extending between the first and second ends, the interior volume being adapted for receiving a steerable catheter. The apparatus also includes a first link member having a proximal end nearest to the anchor and a distal end spaced apart from the proximal end. The proximal end of the first link member is coupled to the anchor by a joint
(Continued)

configured to provide for movement of the first link member in one direction relative to the anchor.

25 Claims, 15 Drawing Sheets

(56) References Cited

U.S. PATENT DOCUMENTS

| | | | |
|---|---|---|---|
| 6,629,534 | B1 | 10/2003 | Goar et al. |
| 6,695,808 | B2 | 2/2004 | Tom |
| 6,752,813 | B2 | 6/2004 | Goldfarb et al. |
| 6,770,083 | B2 | 8/2004 | Seguin |
| 6,793,673 | B2 | 9/2004 | Kowalsky et al. |
| 6,824,562 | B2 | 11/2004 | Mathis et al. |
| 6,960,229 | B2 | 11/2005 | Mathis et al. |
| 6,964,683 | B2 | 11/2005 | Kowalsky et al. |
| 6,976,995 | B2 | 12/2005 | Mathis et al. |
| 7,048,754 | B2 | 5/2006 | Martin et al. |
| 7,179,282 | B2 | 2/2007 | Alferness et al. |
| 7,226,467 | B2 | 6/2007 | Lucatero et al. |
| 7,288,097 | B2 | 10/2007 | Séguin |
| 7,311,729 | B2 | 12/2007 | Mathis et al. |
| 7,316,708 | B2 | 1/2008 | Gordon et al. |
| 7,351,260 | B2 | 4/2008 | Nieminen et al. |
| 7,364,588 | B2 | 4/2008 | Mathis et al. |
| 7,464,712 | B2 | 12/2008 | Oz et al. |
| 7,503,931 | B2 | 3/2009 | Kowalsky et al. |
| 7,563,267 | B2 | 7/2009 | Goldfarb et al. |
| 7,604,646 | B2 | 10/2009 | Goldfarb et al. |
| 7,608,091 | B2 | 10/2009 | Goldfarb et al. |
| 7,655,015 | B2 | 2/2010 | Goldfarb et al. |
| 7,666,204 | B2 | 2/2010 | Thornton et al. |
| 7,674,287 | B2 | 3/2010 | Alferness et al. |
| 7,682,369 | B2 | 3/2010 | Séguin |
| 7,736,388 | B2 | 6/2010 | Goldfarb et al. |
| 7,828,841 | B2 | 11/2010 | Mathis et al. |
| 7,828,842 | B2 | 11/2010 | Nieminen et al. |
| 7,837,728 | B2 | 11/2010 | Nieminen et al. |
| 7,837,729 | B2 | 11/2010 | Gordon et al. |
| 7,857,846 | B2 | 12/2010 | Alferness et al. |
| 7,955,384 | B2 | 6/2011 | Rafiee et al. |
| 8,006,594 | B2 | 8/2011 | Hayner et al. |
| 8,048,063 | B2 | 11/2011 | Aeby et al. |
| 8,062,358 | B2 | 11/2011 | Mathis et al. |
| 8,075,608 | B2 | 12/2011 | Gordon et al. |
| 8,172,898 | B2 | 5/2012 | Alferness et al. |
| 8,182,529 | B2 | 5/2012 | Gordon et al. |
| 8,250,960 | B2 | 8/2012 | Hayner et al. |
| 8,864,757 | B2 | 10/2014 | Klimovitch et al. |
| 9,408,695 | B2 | 8/2016 | Mathis et al. |
| 9,526,613 | B2 | 12/2016 | Gross et al. |
| 2004/0267358 | A1 | 12/2004 | Reitan |
| 2006/0184242 | A1 | 8/2006 | Lichtenstein |
| 2015/0164598 | A1 | 6/2015 | Blumenkranz et al. |

OTHER PUBLICATIONS

Maselli et al., "Percutaneous mitral annuloplasty an anatomic study of human coronary sinus and its relation with mitral valve annulus and coronary arteries," Circulation, vol. 114, No. 5, pp. 377-380, 2006.
Del Valle-Fernández et al., "Insight into the dynamics of the coronary sinus/great cardiac vein and the mitral annulus implications for percutaneous mitral annuloplasty techniques," Circulation: Cardiovascular Interventions, vol. 2 No. 6, pp. 557-564, 2009.
El-Maasarany et al., "The coronary sinus conduit function: anatomical study (relationship to adjacent structures)," Europace, vol. 7, No. 5, pp. 475-481, 2005.
Sorgente et al., "Influence of left atrial and ventricular volumes on the relation between mitral valve annulus and coronary sinus," The American Journal of Cardiology, vol. 102, No. 7, pp. 890-896, 2008.
Sahni et al., "Spatial relationship of coronary sinus-great cardiac vein with adjoining anatomic structures: a key element in predicting the success of percutaneous transvenous mitral annuloplasty." The Journal of Heart Valve Disease, vol. 23, No. 2, pp. 184-192, 2014.
Chiribiri et al., "Magnetic resonance cardiac vein imaging: relation to mitral valve annulus and left circumflex coronary artery," JACC: Cardiovascular Imaging, vol. 1, No. 6, pp. 729-738, 2008.
Mao et al., "Coronary venous imaging with electron beam computed tomographic angiography: three-dimensional mapping and relationship with coronary arteries," American Heart Journal, vol. 150, No. 2, pp. 315-322, 2005.
Shinbane et al., "Anatomic and electrophysiologic relation between the coronary sinus and mitral annulus: implications for ablation of left-sided accessory pathways," American Heart Journal, vol. 135, No. 1, pp. 93-98, 1998.
Lancellotti et al., "European association of echocardiography recommendations for the assessment of valvular regurgitation. part 2: mitral and tricuspid regurgitation (native valve disease)," European Heart Journal—Cardiovascular Imaging, vol. 11, No. 4, pp. 307-332, 2010.
Dwivedi et al., "Reference values for mitral and tricuspid annular dimensions using two-dimensional echocardiography," Journal of Echo Research and Practice, vol. 1, No. 2, pp. 43-50, 2014.
Tops et al., "Noninvasive evaluation of coronary sinus anatomy and its relation to the mitral valve annulus implications for percutaneous mitral annuloplasty," Circulation, vol. 115, No. 11, pp. 1426-1432, 2007.
Plass et al., "Assessment of coronary sinus anatomy between normal and insufficient mitral valves by multi-slice computer tomography for mitral annuloplasty device implantation," European Journal of Cardio-Thoracic Surgery, vol. 33, No. 4, pp. 583-589, 2008.
Choure et al., "In vivo analysis of the anatomical relationship of coronary sinus to mitral annulus and left circumflex coronary artery using cardiac multidetector computed tomography," Journal of the American College of Cardiology, vol. 48, No. 10, pp. 1938-1945, 2006.
Lansac et al., "Percutaneous mitral annuloplasty through the coronary sinus: an anatomic point of view," The Journal of Thoracic and Cardiovascular Surgery, vol. 135, No. 2, pp. 376-381, 2008.
Microlight, "Microlight 3D-Printer", Datasheet, accessed on Aug. 23, 2017 <http://www.microlight.fr/static/assets/img/datasheet.pdf> (2 pages).
Jensen et al., "Saddle-shaped mitral valve annuloplasty rings experience lower forces compared with flat rings," Circulation, vol. 118, No. 14, pp. 250-255, 2008.
Webb et al., "Percutaneous Transvenous Mitral Annuloplasty", Circulation, 2006, 113(6): 851-855.
Sorajja et al., "A Novel Method of Percutaneous Mitral Valve Repair for Ischemic Mitral Regurgitation", JACC: Cardiovascular Interventions, 2008, 1(6): 663-673.
Sack et al., "Percutaneous Transvenous Mitral Annuloplasty: Initial Human Experience With a Novel Coronary Sinus Implant Device", Circulation: Cardiovascular Interventions, 2009, 2(4): 277-284.
Harnek et al., "Transcatheter Implantation of the MONARC Coronary Sinus Device for Mitral Regurgitation: 1-Year Results From the Evolution Phase I Study (Clinical Evaluation of the Edwards Lifesciences Percutaneous Mitral Annuloplasty System for the Treatment of Mitral Regurgitation)," JACC: Cardiovascular Interventions, 2011, 4(1): 115-122.
Pedrazzini et al., "Mitral regurgitation", Swiss Med Wkly, 2010, 140(3-4): 36-43.
Nkomo et al., "Burden of valvular heart diseases: a population-based study", Lancet, 2006, 368(9540): 1005-11.
Maisano et al., "Midterm results of edge-to-edge mitral valve repair without annuloplasty", J. Thorac. Cardiovasc. Surg., 2013, 126(6): 1987-1997.
Fedak et al., "Evolving Concepts and Technologies in Mitral Valve Repair", Circulation, 2008, 117(7): 963-974.
Bonchek et al., "Minimally Invasive Coronary Bypass: A Dissenting Opinion", Circulation, Journal of the American Heart Association, 1999, 98(6): 495-497.
Taghipour et al., "Towards FBG-Based Temperature Independent Force/Torque Sensor for Cardiac Ablation Catheters", International Symposium on Optomechatronics Technology (ISOT), Itabashi, Japan, Nov. 2016.

(56) References Cited

OTHER PUBLICATIONS

Eaton et al., "Innovation in Medical Technology: Ethical Issues and Challenges", Baltimore: The Johns Hopkings University Press, 2007.
Alessandrini et al., "Early results results with the minimally invasive thoracotomy for myocardial revascularization", European Journal of Cardio-Thoracic Surgery, 1997, 11(6): 1081-1085.
Alderman et al., "Five-Year Clinical and Functional Outcome Comparing Bypass Surgery and Angioplasty in Patients With Multivessel Coronary Disease: A Multicenter Randomized Trial", Journal of the American Medical Association (JAMA), 1997, 277(9): 715-721.
Eagle et al., "Practical cardiology: evaluation and treatment of common cardiovascular disorders" Philadelphia: Lippincott Williams & Wilkins, 2008.
Kar, "Percutaneous Transcatheter Mitral Valve Repair", Journal of the American College of Cardiology, 2013, 62(12): 1062-1064.
Chiam et al., "Percutaneous Transcatheter Mitral Valve Repair: A Classification of the Technology", JACC: Cardiovascular Interventions, 2011, 4(1): 1-13.
Fucci et al., "Improved results with mitral valve repair using new surgical techniques", European Journal of Cardio-Thoracic Surgery, 1995, 9(11): 621-626.
Schofer et al., "Percutaneous Mitral Annuloplasty for Functional Mitral Regurgitation: Results of the Carillon Mitral Annuloplasty Device European Union Study", Circulation, 2009, 120(4): 326-333.
Yokoyama et al., "Novel Contact Force Sensor Incorporated in Irrigated Radiofrequency Ablation Catheter Predicts Lesion Size and Incidence of Steam Pop and Thrombus", Circulation: Arrhythmia and Electrophysiology, 2008, 1(5): 354-362.
Rosen et al., "Surgeon-Tool Force/Torque Signatures—Evaluation of Surgical Skills in Minimally Invasive Surgery", in Proceedings of Medicine Meets Virtual Reality, San Francisco, CA, Jan. 1999, pp. 290-296.
Kanagaratnam et al., "Experience of robotic catheter ablation in humans using a novel remotely steerable catheter sheath," Journal of Interventional Cardiac Electrophysiology, 2008, 21(1): 19-26.
Piers et al. "A micro optical force sensor for force feedback during minimally invasive robotic surgery", Sensors and Actuators A: Physical, 2004, 115(2): 447-455.
Polygerinos et al., "Novel Miniature MRI-Compatible Fiber-Optic Force Sensor for Cardiac Catheterization Procedures", in IEEE International Conference on Robotics and Automation (ICRA), Anchorage, AK, May 2010, pp. 2598-2603.
Polygerinos et al., "Triaxial Catheter-Tip Force Sensor for MRI-Guided Cardiac Procedures", IEEE/ASME Transactions on Mechatronics, 2013, 18(1): 386-396.
Eick, "Temperature Controlled Radiofrequency Ablation", Indian Pacing and Electrophysiology Journal, 2002, 2(3): 66-73.
Arata et al., "Fiber optic force sensor for medical applications within a backbone-shape structure", Procedia CIRP, 2013, 5: 66-69.
Iordachita et al., "A sub-millimetric, 0.25 mn resolution fully integrated fiber-optic force-sensing tool for retinal microsurgery", International Journal of Computer Assisted Radiology and Surgery, 2009, 4(4): 383-390.
Noh et al., "Image-based Optical Miniaturized Three-Axis Force Sensor for Cardiac Catheterization", IEEE Sensors Journal, 2016, 16(22): 7924-7932.
Xu et al., "Temperature-Insensitive Fiber-Optic Contact Force Sensor for Steerable Catheters", IEEE Sensors Journal, 2016, 16(12): 4771-4775.

Ray, "The echocardiographic assessment of functional mitral regurgitation", European Heart Journal-Cardiovascular Imaging, 2010, 11(10): i11-i17.
Lee et al., "Quantitative Analysis of Mitral Valve Morphology in Mitral Valve Prolapse With Real-Time 3-Dimensional Echocardiography: Importance of Annular Saddle Shape in the Pathogenesis of Mitral Regurgitation", Circulation, 2012, 112: 1-23.
Topol et al., "Textbook of Cardiovascular Medicine", Philadelphia: Lippincott Williams & Wilkins, 2007.
Kuwahara et al., "Abstract 19873: Relationship Between Jet Direction and Mitral Valve Tethering in Patients With Ischemic Mitral Regurgitation: Real-Time Three Dimensonal Transesophageal Echocardiography Study", Circulation, 2010, 122(suppl 21): A19873.
Buchner et al., "Direct Visualization of Regurgitant Orifice by CMR Reveals Differential Asymmetry According to Etiology of Mitral Regurgitation", JACC: Cardiovascular Imaging, 2011, 4(10): 1088-1096.
Marsan et al., "Quantification of Functional Mitral Regurgitation by Real-Time 3D Echocardiography: Comparison With 3D Velocity-Encoded Cardiac Magnetic Resonance", JACC: Cardiovascular Imaging, 2009, 2(11): 1245-1252.
Magne et al., "Exercise Pulmonary Hypertension in Asymptomatic Degenerative Mitral Regurgitation", Circulation, 2010, 122(1): 33-41.
Rack et al., "Titanium alloys for biomedical applications", Materials Science and Engineering: C, 2006, 26(8): 1269-1277.
Stein et al., "Measured Turbulence and Its Effect on Thrombus Formation", Circulation Research, 1974, 35(4): 608-614.
Fogel et al., "Ventricular Function and Blood Flow in Congenital Heart Disease", Hoboken: Wiley, 2008.
Mohl et al., "PICSO: from myocardial salvage to tissue regeneration", Cardiovascular Revascularization Medicine, 2015, 16(1): 36-46.
Ganz et al., "Measurement of Coronary Sinus Blood Flow by Continuous Thermodilution in Man", Circulation, 1971, 44(2): 181-195.
Bloch et al., "Quantifying coronary sinus flow and global LV perfusion at 3T", BMC medical imaging, 2009, 9(1): 9 (13 pages).
Costanzo, "Physiology E-Book", Amsterdam, Netherlands: Elsevier Health Sciences, 2017.
Perna et al., "Assessment of Catheter Tip Contact Force Resulting in Cardiac Perforation in Swine Atria Using Force Sensing Technology", Circulation: Arrhythmia and Electrophysiology, 2011, 4(2): 218-224.
Sarkozy et al., "Contact Force in Atrial Fibrillation: Role of Atrial Rhythm and Ventricular Contractions", Circulation: Arrhythmia and Electrophysiology, 2015, 8(6): 1342-1350.
Akay, "Introduction to Polymer Science and Technology", Bookboon, Mustafa Akay & Ventus Publishing ApS, 2012 <https://books.google.ca/books?id=1J1k7cGYTWcC>.
Srivatsan et al., "Additive Manufacturing: Innovations, Advances, and Applications", Boka Raton: CRC Press, 2015.
"F/T Transducer: Six-Axis Force/Torque Sensor system Installation and Operation Manual", ATI Industrial Automation, Apex, NC, 2016, pp. 1-142 <https://www.ati-ia.com/app_content/documents/9620-05-Transducer%20Section.pdf>.
Delling et al., "Epidemiology and Pathophysiology of Mitral Valve Prolapse: New Insights Into Disease Progression, Genetics, and Molecular Basis", Circulation, 2014, 129(21): 2158-2170.
Tamburino et al., "Percutaneous Treatment of Left Side Cardiac Valves: A Practical Guide for the Interventional Cardiologist", Berlin, Germany: Springer Science & Business Media, 2012.

* cited by examiner

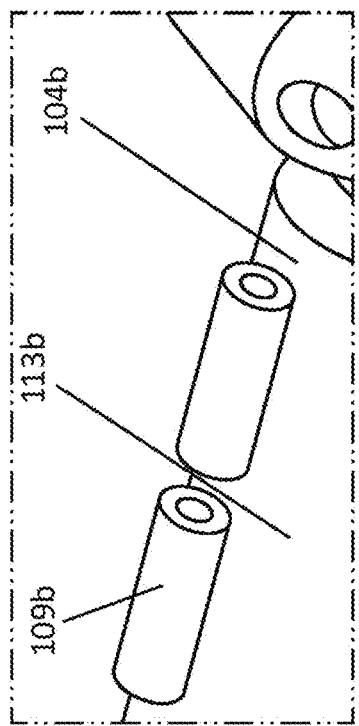
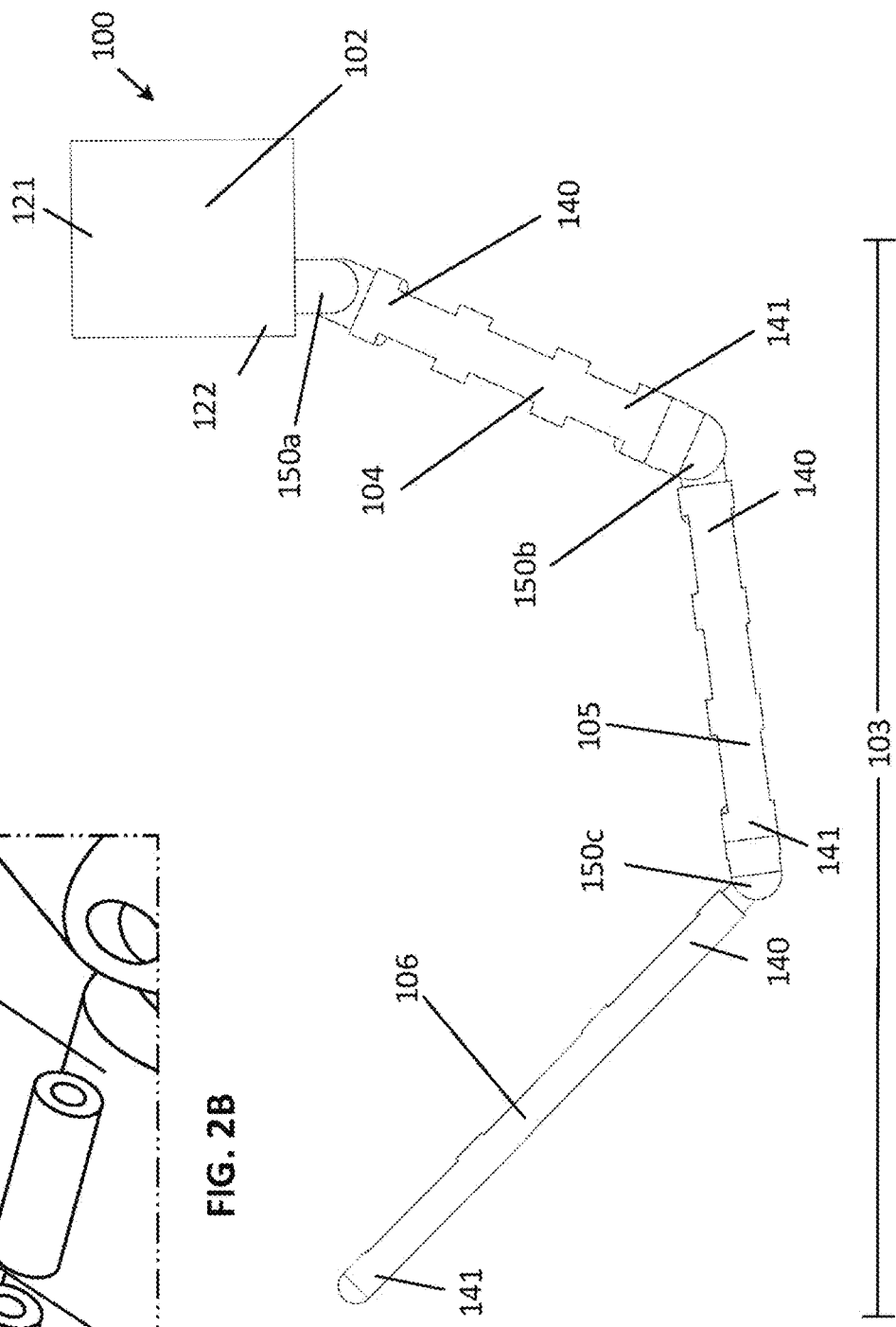

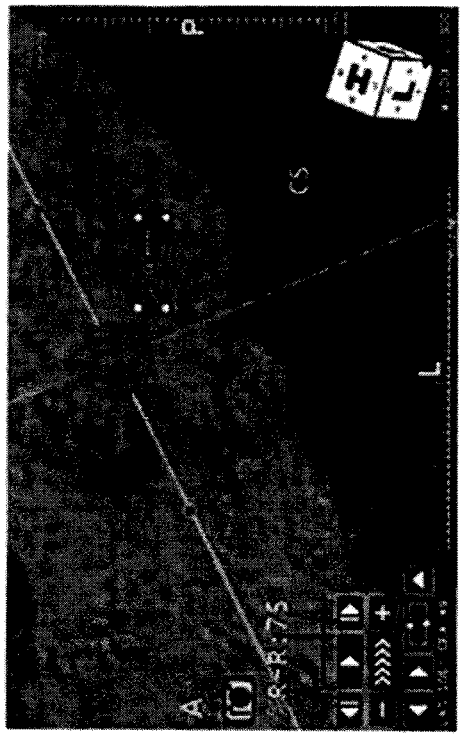
FIG. 14B
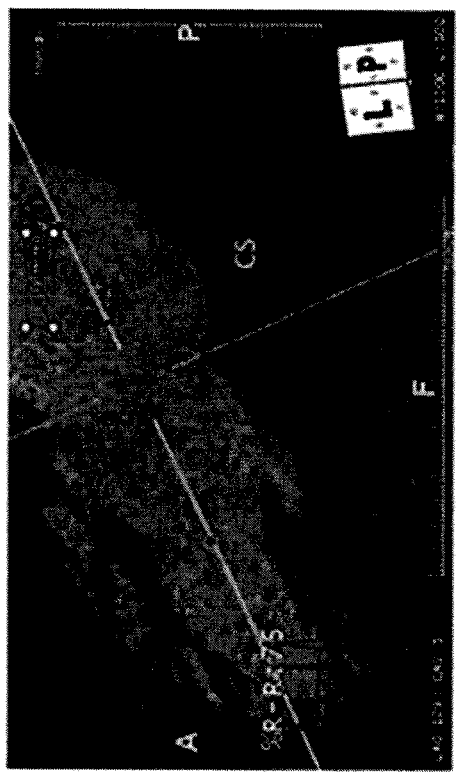
FIG. 14A
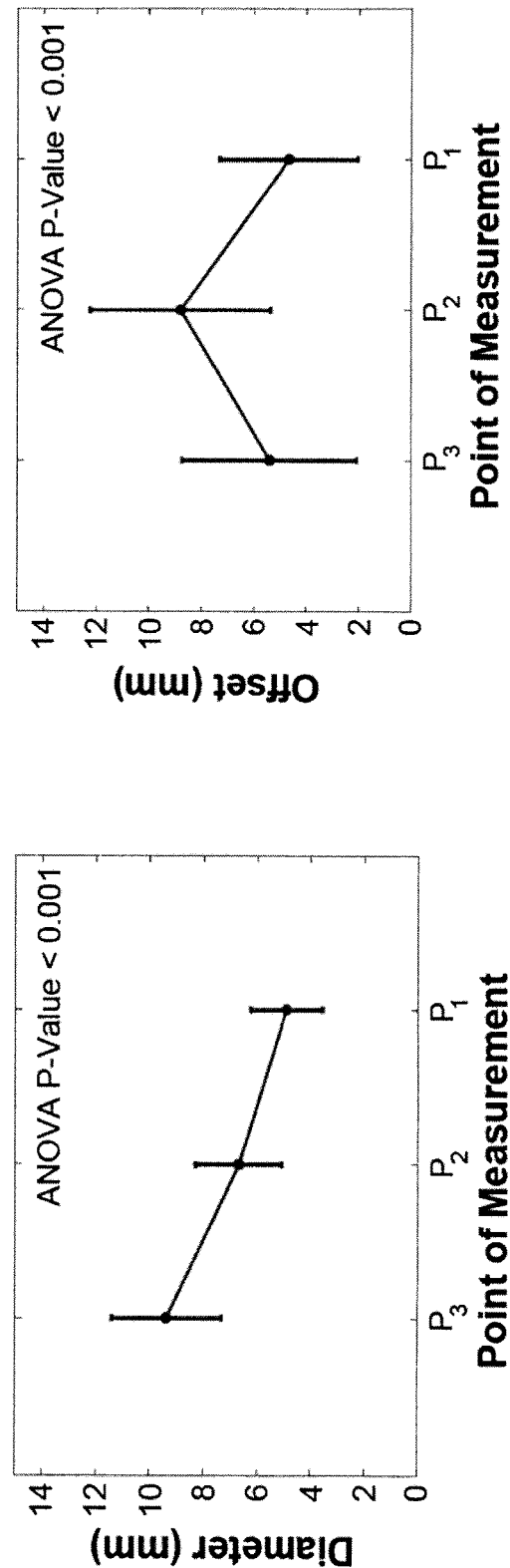
FIG. 15B
FIG. 15A

APPARATUS AND SYSTEM FOR CHANGING MITRAL VALVE ANNULUS GEOMETRY

CROSS-REFERENCE

This application is a 35 USC § 371 national stage entry of International Patent Application No. PCT/CA2018/051116, filed Sep. 11, 2018, which claims the benefit of U.S. Provisional Patent Application No. 62/557,349, filed Sep. 12, 2017, and entitled "APPARATUS AND SYSTEM FOR CHANGING MITRAL VALVE ANNULUS GEOMETRY"; the entire contents of each of which are hereby incorporated by reference.

FIELD

This disclosure relates generally to an apparatus and system for changing geometry of a heart valve structure, and more specifically to an apparatus and system for changing mitral valve annulus geometry through the coronary sinus vein.

BACKGROUND

The mitral valve is located in the left atrial ventricular opening between the left atrium and left ventricle. The mitral valve provides for oxygenated blood to flow from the left atrium to the left ventricle for distribution throughout the body. The structure of the mitral valve includes posterior and anterior leaflets that are surrounded by a mitral valve annulus. Chordae tendineae are thin fibrous strings connecting the posterior and anterior leaflets to papillary muscles that, upon contraction of the left ventricle, close the mitral valve. Correspondingly, relaxation of the left ventricle opens the mitral valve. A healthy mitral valve is able to withstand considerable back pressure and prevent regurgitation of blood from the left ventricle back into the left atrium as the left ventricle contracts.

Mitral valve regurgitation is a heart disease that can arise from a variety of different circumstances. For example, certain diseases may cause dilation of the mitral valve annulus. This can result in deformation of the mitral valve geometry to cause ineffective closure of the mitral valve during left ventricular contraction. Such ineffective closure results in leakage through the mitral valve and regurgitation. Diseases such as bacterial inflammations of the heart or heart failure can cause the aforementioned distortion or dilation of the mitral valve annulus.

Several technologies have been developed that attempt to correct distortion or dilation of the mitral valve annulus. Some of these technologies consist of devices introduced into the coronary sinus vein to reduce the diameter of the mitral annulus for improving ineffective closure of the valve.

However, one potential consequence of this mode of treatment using conventional means is the compression of the left circumflex artery as it crosses the left atrioventricular groove, which can reduce perfusion of blood to portions of the heart supplied by the left circumflex artery.

SUMMARY

In accordance with one broad aspect of the teachings herein, there is provided an apparatus for changing a geometry of a mitral valve annulus of a heart, the apparatus comprising: an anchor having a body configured to be positioned within and anchored to a coronary sinus vein of the heart, the body having: a first end and a second end, the first end spaced apart from the second end; a longitudinally extending axis; and a wall with an interior volume extending from the first end to the second end, the interior volume being adapted for receiving a steerable catheter; and a first link member having a proximal end nearest to the anchor and a distal end spaced apart from the proximal end, the proximal end of the first link member being coupled to the first end of the anchor by a first joint configured to provide for movement of the first link member in one direction relative to the anchor.

In at least one embodiment, a second link member is provided, the second link member having a proximal end nearest to the anchor and a distal end spaced apart from the proximal end, the proximal end of the second link member being coupled to the distal end of the first link member by a second joint configured to provide for movement of the second link member in one direction relative to the first link member.

In at least one embodiment, one or more additional link members are provided, each additional link member having a proximal end nearest the anchor and a distal end spaced apart from the proximal end, the proximal end of each additional link member being coupled to the distal end of an adjacent link member nearer to the anchor by an additional joint configured to provide for movement of the additional link member relative to the adjacent link member in one direction relative to the adjacent link member.

In at least one embodiment, the first link member is movably coupled to the anchor by a first actuating tendon and a first release tendon such that actuation of the first actuating tendon controls the movement of the first link member in a first direction towards the mitral valve annulus to apply a first force to the mitral valve annulus.

In at least one embodiment, the first joint is configured as a ratchet having a first pawl and a first plurality of teeth, the first release tendon coupled to the first pawl to release the first pawl from the first plurality of teeth.

In at least one embodiment, the second link member is movably coupled to the anchor by a second actuating tendon and a second release tendon such that actuation of the second actuating tendon controls the movement of the second link member in a second direction towards the mitral valve annulus to apply a second force to the mitral valve annulus.

In at least one embodiment, the second joint is configured as a second ratchet having a second pawl and a second plurality of teeth, the second release tendon coupled to the second pawl to release the second pawl from the second plurality of teeth.

In at least one embodiment, the first actuating tendon is coupled to the distal end of the first link member and the second actuating tendon is coupled to the distal end of the second link member.

In at least one embodiment, the first actuating tendon has a first end positioned inside of a first channel of the anchor.

In at least one embodiment, the first end of the first actuating tendon is sized and shaped to be retained in the first channel.

In at least one embodiment, the first end of the first actuating tendon is sized and shaped to provide for a grabbing portion of the steerable catheter to grab the first end to actuate the first actuating tendon.

In at least one embodiment, the first actuating tendon extends through a tendon support of the first link member towards the distal end of the first link member.

In at least one embodiment, the second actuating tendon extends through the tendon support of the first link member towards the distal end of the second link member.

In accordance with another broad aspect of the teachings herein, there is provided a system for changing a geometry of a mitral valve annulus of a heart, the system comprising: an apparatus comprising: an anchor having a body configured to be positioned within and anchored to a coronary sinus vein of the heart, the body having: a first end and a second end, the first end spaced apart from the second end; a longitudinally extending axis; and a wall having an interior volume extending from the first end to the second end; a first link member having a proximal end nearest to the anchor and a distal end spaced apart from the proximal end, the proximal end of the first link member being coupled to the first end of the anchor by a first joint configured to provide for movement of the first link member in one direction relative to the anchor; and a steerable catheter comprising: a catheter body; and a sub-catheter extending from the catheter body, the sub-catheter being adapted to engage the first link member when the sub-catheter is positioned in the interior volume of the anchor of the apparatus.

In at least one embodiment, the sub-catheter has a grabbing portion for engaging an actuating tendon of the first link member when the sub-catheter is positioned in the interior volume of the anchor of the apparatus.

In at least one embodiment, when the apparatus comprises additional link members, the grabbing portion of the sub-catheter is also configured to engage the additional link members.

In at least one embodiment, the apparatus further comprises a second link member having a proximal end nearest to the anchor and a distal end spaced apart from the proximal end, the proximal end of the second link member being movably coupled to the distal end of the first link member by a second joint configured to provide for movement of the second link member in one direction relative to the first link member.

In at least one embodiment, the first link member is movably coupled to the anchor by a first actuating tendon and a first release tendon such that actuation of the first actuating tendon controls the movement of the first link member in a first direction towards the mitral valve annulus to apply a first force to a portion of the mitral valve annulus.

In at least one embodiment, upon engaging the first actuating tendon, movement of the sub-catheter controls the movement of the first link member in a direction towards the mitral valve annulus to control a magnitude of the first force applied to a portion of the mitral valve annulus by controlling a position of the first link member with respect to the portion of the mitral valve annulus.

In at least one embodiment, the anchor further comprises a tendon channel and the sub-catheter engages the first actuating tendon within the tendon channel.

In at least one embodiment, the anchor further comprises a guiding rail having an opening and the catheter body comprises a guiding channel, the guiding channel being sized and shaped to guide the guiding rail to align the sub-catheter into the tendon channel as the sub-catheter extends into the anchor.

In accordance with another broad aspect of the teachings herein, there is provided a steerable catheter for engaging an apparatus, described in accordance with any of the teachings herein, for changing mitral valve geometry of a heart. The steerable catheter includes a catheter body and a sub-catheter extending from the catheter body. The sub-catheter has a grabbing portion for engaging a tendon of the apparatus when the sub-catheter is inserted into an interior volume of an anchor of the apparatus.

In at least one embodiment, the grabbing portion extends from the sub-catheter to engage a tendon head to engage the tendon.

In at least one embodiment, the grabbing portion is complementary in shape to the tendon head to engage the tendon head.

In at least one embodiment, the steerable catheter further comprises a guiding channel configured to receive a guiding rail of the anchor of the apparatus to align the sub-catheter with the tendon when the sub-catheter is inserted into an interior volume of an anchor of the apparatus.

In accordance with another broad aspect of the teachings herein, there is provided a method of changing a geometry of a mitral valve annulus of a heart. The method includes implanting an apparatus into a coronary sinus vein of the heart, the apparatus including an anchor having a body, the body having a first end and a second end, the first end spaced apart from the second end; a longitudinally extending axis; and a wall having an interior volume extending from the first end to the second end. The apparatus also includes a first link member having a proximal end nearest to the anchor and a distal end spaced apart from the proximal end, the proximal end of the first link member being movably coupled to the first end of the anchor by a first joint configured to provide for movement of the first link member in one direction relative to the anchor. The method also includes adjusting the apparatus with a steerable catheter, the steerable catheter comprising a catheter body; and a sub-catheter extending from the catheter body, the sub-catheter engaging the first link member when the sub-catheter is positioned in the interior volume of the anchor of the apparatus to adjust a position of the first link member to apply a force against the mitral valve to change the geometry of the mitral valve annulus.

In at least one embodiment, the method further comprises using a grabbing portion of the sub-catheter to engage the first link member when the sub-catheter is inserted into the interior volume of the anchor.

In at least one embodiment, when the apparatus comprises additional link members, the method further comprises using the grabbing portion of the sub-catheter to engage the additional link members.

In at least one embodiment, the adjustment of the apparatus occurs: (a) immediately after implantation of the apparatus, (b) during a same surgical procedure as the implanting the apparatus or (c) during a subsequent surgical procedure after the procedure for the implanting the apparatus.

These and other features and advantages of the present application will become apparent from the following detailed description taken together with the accompanying drawings. It should be understood, however, that the detailed description and the specific examples, while indicating preferred embodiments of the application, are given by way of illustration only, since various changes and modifications within the spirit and scope of the application will become apparent to those skilled in the art from this detailed description.

BRIEF DESCRIPTION OF THE DRAWINGS

For a better understanding of the various embodiments described herein, and to show more clearly how these various embodiments may be carried into effect, reference will be made, by way of example, to the accompanying drawings which show at least one example embodiment, and which are now described. The drawings are not intended to limit the scope of the teachings described herein.

FIG. 2B is a magnified view of a portion of the apparatus of FIG. 2A.

FIG. 3 is a top view of the apparatus of FIG. 2A.

FIG. 14A is a CT scan showing the measurement of coronary sinus diameter at P3.

FIG. 14B is a CT scan showing an example for measurement of coronary sinus offset from the mitral annulus at P2 (shown on FIG. 12B).

FIG. 15A is a graph showing coronary sinus diameter measurements at points P1, P2 and P3.

FIG. 15B is a graph showing coronary sinus offset measurements at points P1, P2 and P3.

Figure 1A:
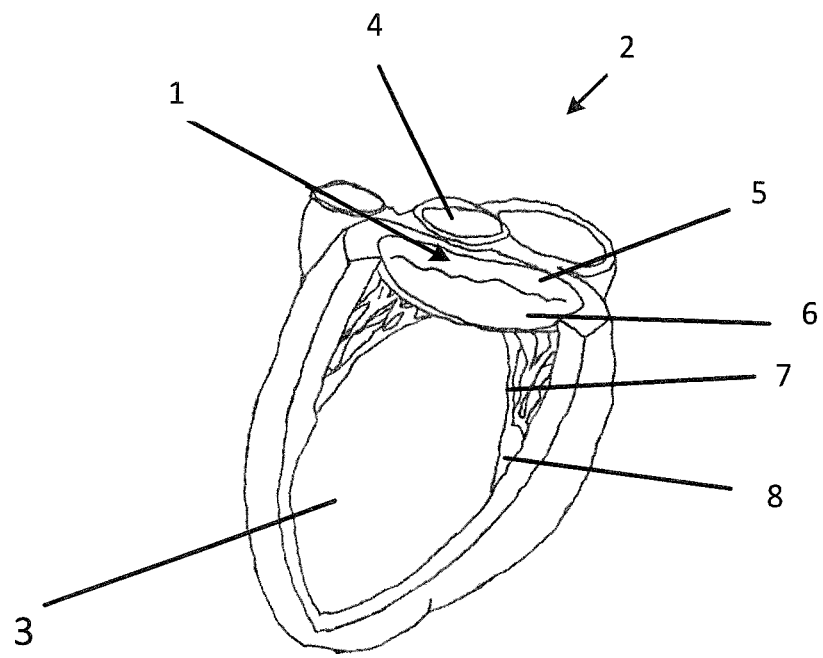
FIG. 1A is a cross-section view of a portion of a heart showing the mitral valve and related structures.

Further aspects and features of the example embodiments described herein will appear from the following description taken together with the accompanying drawings.

DESCRIPTION OF EXAMPLE EMBODIMENTS

Various apparatuses, methods and compositions are described below to provide an example of at least one embodiment of the claimed subject matter. No embodiment described below limits any claimed subject matter and any claimed subject matter may cover apparatuses and methods that differ from those described below. The claimed subject matter are not limited to apparatuses, methods and compositions having all of the features of any one apparatus, method or composition described below or to features common to multiple or all of the apparatuses, methods or compositions described below. It is possible that an apparatus, method or composition described below is not an embodiment of any claimed subject matter. Any subject matter that is disclosed in an apparatus, method or composition described herein that is not claimed in this document may be the subject matter of another protective instrument, for example, a continuing patent application, and the applicant(s), inventor(s) and/or owner(s) do not intend to abandon, disclaim, or dedicate to the public any such invention by its disclosure in this document.

Furthermore, it will be appreciated that for simplicity and clarity of illustration, where considered appropriate, reference numerals may be repeated among the figures to indicate corresponding or analogous elements. In addition, numerous specific details are set forth in order to provide a thorough understanding of the example embodiments described herein. However, it will be understood by those of ordinary skill in the art that the example embodiments described herein may be practiced without these specific details. In other instances, well-known methods, procedures, and components have not been described in detail so as not to obscure the example embodiments described herein. Also, the description is not to be considered as limiting the scope of the example embodiments described herein.

It should be noted that terms of degree such as "substantially", "about" and "approximately" as used herein mean a reasonable amount of deviation of the modified term such that the end result is not significantly changed. These terms of degree should be construed as including a deviation of the modified term, such as 1%, 2%, 5%, or 10%, for example, if this deviation would not negate the meaning of the term it modifies.

Furthermore, the recitation of any numerical ranges by endpoints herein includes all numbers and fractions subsumed within that range (e.g. 1 to 5 includes 1, 1.5, 2, 2.75, 3, 3.90, 4, and 5). It is also to be understood that all numbers and fractions thereof are presumed to be modified by the term "about" which means a variation up to a certain amount of the number to which reference is being made, such as 1%, 2%, 5%, or 10%, for example, if the end result is not significantly changed.

It should also be noted that, as used herein, the wording "and/or" is intended to represent an inclusive-or. That is, "X and/or Y" is intended to mean X or Y or both, for example. As a further example, "X, Y, and/or Z" is intended to mean X or Y or Z or any combination thereof.

The following description is not intended to limit or define any claimed or as yet unclaimed subject matter. Subject matter that may be claimed may reside in any combination or sub-combination of the elements or process steps disclosed in any part of this document including its claims and figures. Accordingly, it will be appreciated by a person skilled in the art that an apparatus, system or method disclosed in accordance with the teachings herein may embody any one or more of the features contained herein and that the features may be used in any particular combination or sub-combination that is physically feasible and realizable for its intended purpose.

In spite of the technologies that have been developed, there remains a need in the field for improvements in the development of apparatuses for changing mitral valve annulus geometry. In accordance with the teachings herein, various embodiments are described for an apparatus and method that is adjustable and re-configurable over time for changing mitral valve annulus geometry within a heart.

Referring now to FIG. 1A, illustrated therein is a cross-section view of the heart showing the mitral valve and its main parts. Specifically, the mitral valve 1 is a valve inside of the heart 2 that is located between the left atrium (not shown) and the left ventricle 3. The mitral valve 1 opens during diastole to provide for blood to flow from the left atrium to the left ventricle 3 and subsequently through the aorta 4 to the body. The mitral valve 1 closes in ventricle systole inhibiting blood from flowing back into the left atrium from the left ventricle 3. The mitral valve 1 includes an anterior mitral leaflet 5, a posterior mitral leaflet 6, chordae tendineae 7, papillary muscles 8 and a mitral valve annulus 10 (shown in FIGS. 1A and 1B).

Figure 1B:
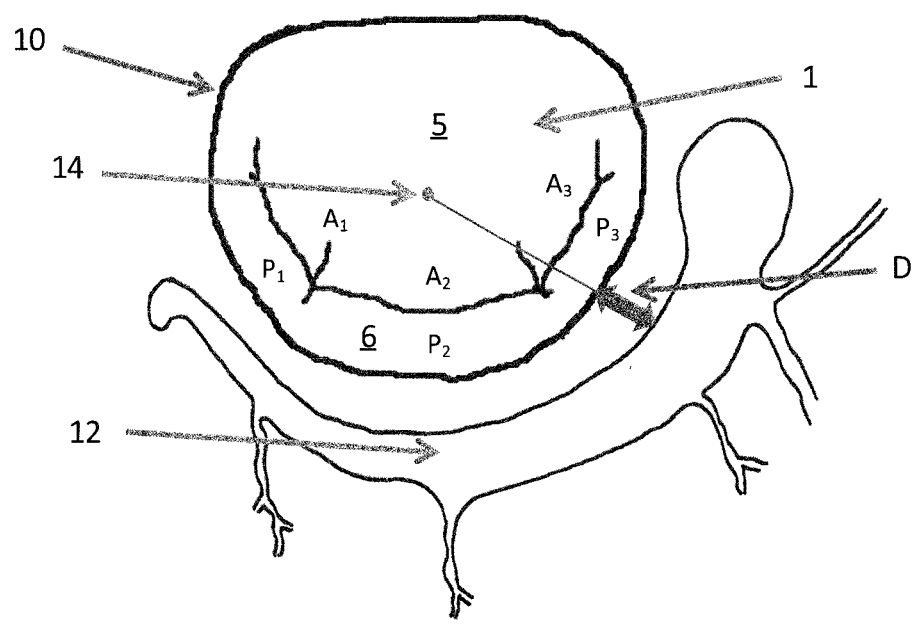
FIG. 1B is an atrial view of the mitral valve and the coronary sinus.

Referring now to FIG. 1B, illustrated therein is an atrial view (e.g. top-down) of the mitral valve 1 and the coronary sinus 12. The mitral valve annulus 10 is a D-shaped fibrous ring that holds the anterior leaflets 5 and posterior leaflets 6 which are thin, pliable and soft textures. The leaflets 5, 6 are like veils with fixed edges that are connected to the mitral valve annulus 10 at one end and have free edges at their other end. The free edges of the two leaflets co-operate (e.g. overlap) to close the mitral valve 1. Posterior leaflet 6 is divided into three scallop-like sections: P1, P2, and P3. Anterior leaflet 5 includes three sections: A1, A2, and A3. Mitral valve 1 is shown as being anterior to coronary sinus 12 by a distance D.

Returning to FIG. 1A, the chordae tendineae 7 are thin fibrous strings that have one end connected to papillary muscles 8 while the other end is attached to one of the anterior and posterior leaflets 5,6. Papillary muscles 8 move the anterior 5 and posterior 6 leaflets with chordae tendineae 7 so the mitral valve 1 can open and close.

Figure 2A:
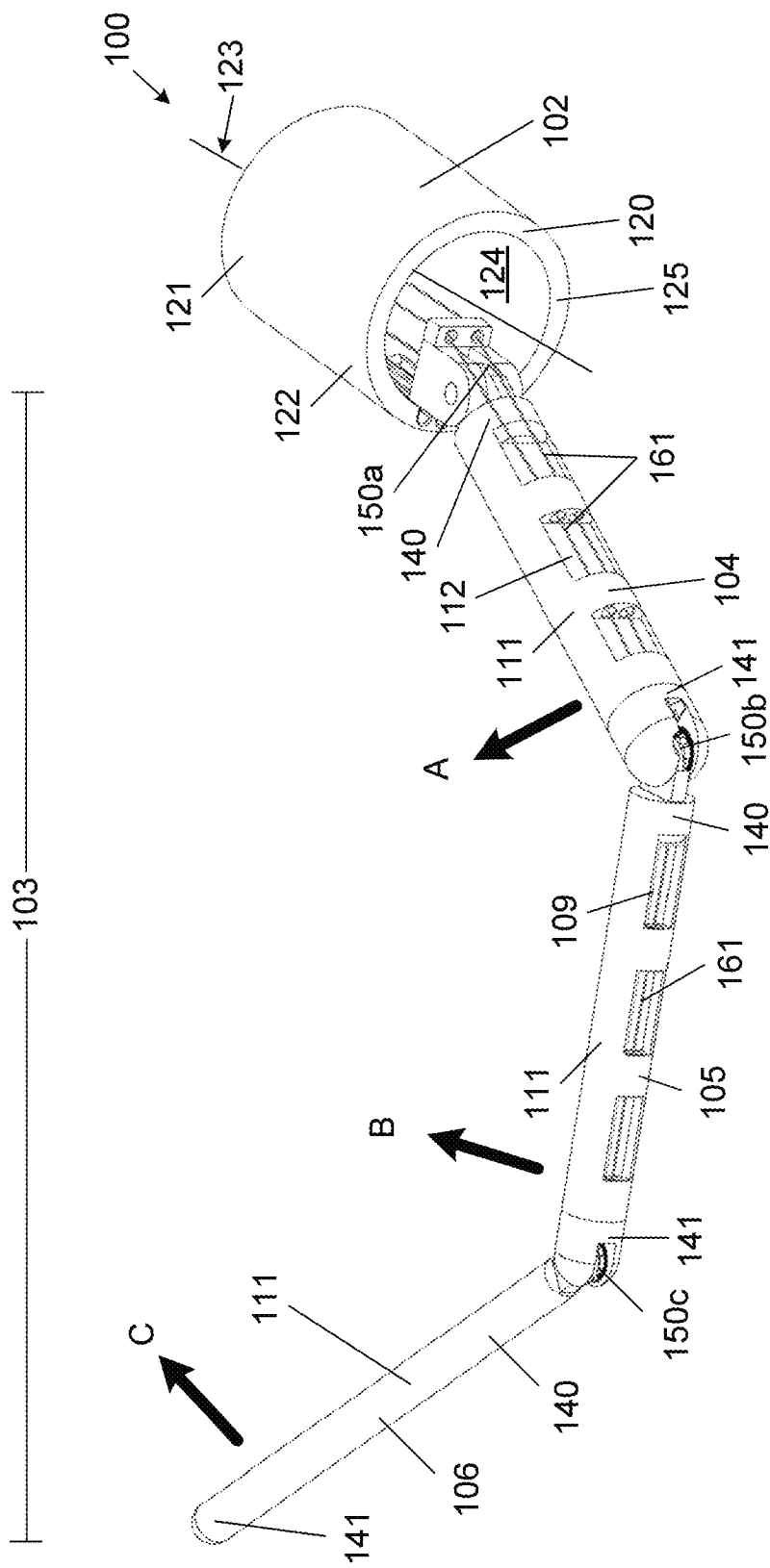
FIG. 2A is a perspective view of an apparatus for use in changing mitral valve annulus geometry, according to one example embodiment.
Figure 4:
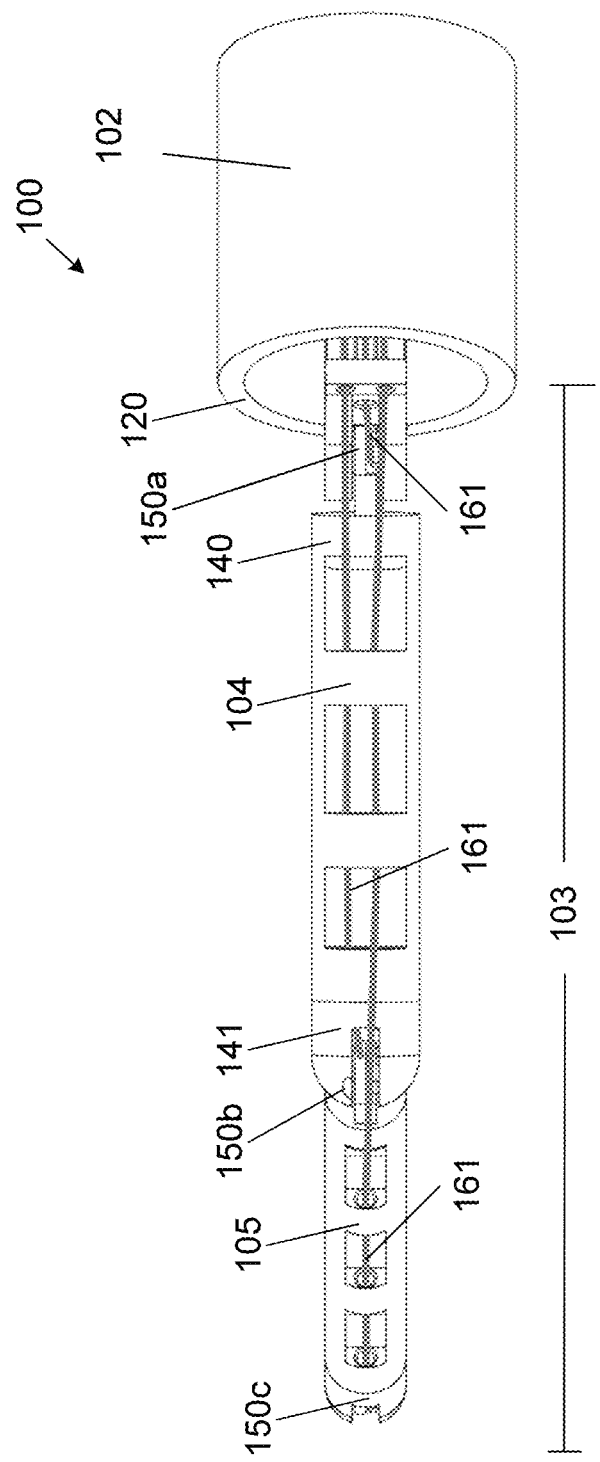
FIG. 4 is a side view of the apparatus of FIG. 2A.

Referring now to FIG. 2A, illustrated therein is an apparatus 100 for changing mitral valve annulus geometry within a heart. Apparatus 100 includes: an anchor 102 for anchoring the apparatus 100 to an interior structure of the heart (e.g. coronary vein), and a plurality of link members 103 for extending through an internal heart structure and applying a pressure and/or a force to a portion of the mitral valve annulus to change the geometry of the mitral valve annulus. In the example embodiment shown in the figures, apparatus 100 includes three link members 104, 105, and 106, with each link member corresponding to a respective section P1, P2 and P3 of the posterior leaflet 6 of the mitral valve annulus 10. In this example embodiment, each link member 104, 105, 106 can be configured to apply a force on a respective section of the posterior leaflet 6 for changing the mitral valve annulus geometry.

Although the apparatus 100 of FIG. 2A is shown as having three link members 104, 105, and 106, in other embodiments apparatus 100 may include more or less than three link members to change mitral valve annulus geometry within a heart. For example, apparatus 100 may have one or two link members coupled to an anchor 102. When apparatus 100 has less than three link members, the tunability (i.e. the ability to apply different pressures and/or forces to different points of the mitral valve annulus to change the geometry of the mitral valve annulus) of apparatus 100 may be reduced when compared to the tunability of the example apparatus 100 that has 3 links as shown in the figures. Further, in some embodiments apparatus 100 may have more than three link members coupled to anchor 102. When apparatus 100 has more than three link members, the tunability of apparatus 100 may be enhanced when compared to the tunability of the example apparatus 100 shown in the figures.

Link members 104, 105, and 106 can each have the same size (e.g. diameter and/or length) or can have different sizes. For example, the diameter of the link members can progressively decrease along the apparatus as the link members are positioned further away from anchor 102 (i.e. link members that are further away from anchor 102 can get progressively smaller and have smaller diameters than adjacent link members that are closer to anchor 102). For instance, as shown in the figures, the diameter of link member 105 can be smaller than the diameter of link member 104, and the diameter of link member 106 can be smaller than the diameter of link member 105. In this way, the diameters of the link members can be configured to correspond to the decreasing diameter of the coronary sinus as the coronary sinus extends from the coronary sinus ostium.

Anchor 102 is situated in an interior structure of the heart to anchor apparatus 100 to an interior structure of the heart. In the example embodiments shown in the figures, anchor 102 is intended to be implanted in the ostium of coronary sinus vein of the heart. In this manner, the geometry of the coronary sinus ostium can provide for the placement and adjustment of the apparatus 100 with a steerable catheter (as described below).

Anchor 102 includes a body 120 having a first end 121, a second end 122 and a longitudinal axis 123. Second end 122 is spaced apart from first end 121 and body 120 is hollow and has an interior volume 124 defined by an inner wall 125.

Anchor 102 is configured to be implanted in an interior structure of the heart to anchor the apparatus 100 while being used to change the geometry of the mitral valve annulus. For instance, in one example embodiment, anchor 102 can be configured such that body 120 is a self-expandable, transcatheter stent having an expanded state and a compressed state. In the compressed state, body 120 may be inserted into a structure (e.g. a vein) distal to the heart (e.g. in a leg or an arm of the patient) and maneuvered through a series of veins of the patient into a position in an interior structure of the heart. In one example embodiment, the interior structure of the heart is the coronary sinus vein. In the expanded state, body 120 may exert a force outwards (e.g. a radial force) from the wall 125 in a direction towards a wall of the interior structure of the heart. In a specific embodiment, anchor 102 is implantable into the coronary sinus ostium of the heart. Further, in the expanded state, anchor 102 supports extension of the plurality of link members 103 longitudinally from anchor 102 along an internal structure of the heart (e.g. the coronary sinus vein) for changing the geometry of the mitral valve annulus.

In the example embodiment shown in FIGS. 2A-4, anchor 102 is shown as an elongated cylinder having a compressed state (not shown) and an expanded state (see FIGS. 2A-4). Anchor 102 is sized and shaped for implantation in the coronary sinus ostium of the heart. It will be appreciated that an anchor 102 having a differing shape and/or size beyond that shown herein may alternatively (or additionally) be provided.

Each link member (e.g. link members 104, 105, and 106) of the plurality of link members 103 has a proximal end 140 and a distal end 141. Proximal end 140 of each link member 104, 105, and 106 of the plurality of link members 103 is defined as the end nearest to anchor 102. Distal end 141 is spaced from and opposed to proximal end 140.

The plurality of link members 103 are coupled to and extend longitudinally from anchor 102. In the example embodiment shown in FIGS. 2A-4, a first link member 104 is coupled to anchor 102 such that proximal end 140 of first link member 104 is coupled to second end 122 of body 120 of anchor 102 via a joint 150. One end of the joint is mounted to inner wall 125 of anchor 102.

Each link member 104, 105, and 106 of the plurality of link members 103 may have one or more tendon supports 109 for supporting tendons connecting anchor 102 to each of the link members 104, 105, and 106. Tendon supports 109 can take many different forms. For example, tendon supports 109 can be integral with a body 111 of each of the link members 104, 105, and 106 (as shown in FIGS. 2A-4) and can be positioned on an internal surface defined by a recessed wall 112 of body 111. In this configuration, tendon supports 109 can support tendons passing there through and protect the tendons from potential damage caused by debris passing by the respective link member. Further, tendon supports 109 can be configured to support a plurality of tendons. For example, as shown in FIGS. 2A-4, tendon supports 109 of link member 104 are configured to support at least two tendons, whereas tendon supports 109 of link member 105 are configured to support one tendon. Generally, tendon supports 109 of link members directly coupled to anchor 102 will support more tendons that tendon supports 109 of link members that are not directly coupled to anchor 102 since the tendons that operate with link members distal to anchor 102 (e.g. link member 104) do not need to extend to proximal to anchor 102 (e.g. link members 105 or 106).

In another example, tendon supports 109 can extend radially from link members 104, 105, and 106 to support the tendons. An example of this configuration is shown in FIG. 2B, where tendon supports 109b extend from and are integral with an outer surface 113b of a link member 104b.

As shown in FIGS. 2A and 3, each link member 104, 105, and 106 of the plurality of link members 103 can have an elongated cylindrical shape to extend into a coronary structure of the heart. In one embodiment, each link member 104, 105, and 106 of the plurality of link members 103 can have an elongated cylindrical shape to extend into the coronary sinus vein of the heart to impart a force on the mitral valve annulus. The link members 104, 105, and 106 may have a circular or elliptical cross-sectional shape to mimic the cross-sectional shape of the coronary sinus. It will be appreciated that link members having differing shapes and sizes beyond those shown in the figures may be alternatively (or additionally) provided.

As shown in FIGS. 2A-4, each of the plurality of link members 103 is coupled to an adjacent link member via a joint 150. For example, proximal end 140 of first link member 104 is coupled to second end of anchor 102 via a first joint 150a, distal end 141 of first link member 104 is coupled to proximal end 140 of second link member 105 via a second joint 150b, and distal end 141 of second link member 105 is coupled to proximal end 140 of third link member 106 via a third joint 150c. In this embodiment, distal end 141 of third link member 106 is a free end that is not coupled to an adjacent link member.

In one example embodiment, each of the link members 104, 105, and 106 can be made of any appropriate biocompatible metallic or polymeric material such as but not limited to a titanium alloy, cobalt-based alloys, stainless steel or any biocompatible polymeric material, or any appropriate combination of these materials.

In the example embodiments shown in the figures, the mechanism of each joint 150a, 150b and 150c is similar to other joints in that each joint includes a ratchet mechanism that is configured to move in one-direction. The shape of joint 150a varies from the shape of joints 150b and 150c as joint 150a couples anchor 102 to the proximate end of link member 104 whereas the second joint 150b and the third joint 150c each couple two adjacent link members (e.g. link members 104 to 105 and 105 to 106, respectively). It should be noted that the ratchet mechanism described herein is one example mechanism of joints 150a, 150b and 150c that can be used to provide for movement of link members 104, 105, 106 in one direction. Any appropriate mechanism of joints 105a, 150b and 1050c can be provided for controlling the movement of the link members 104, 105, 106 in one direction.

Each joint 150a, 150b and 150c restricts movement of a distal component (e.g. a link member) relative to a proximal component (e.g. a link member or anchor 102). For example, in the example embodiment of apparatus 100 shown in FIGS. 2A-4, joint 150a can provide for movement (e.g. rotation) of link member 104 relative to anchor 102. In this regard, joint 150a can provide for link member 104 to rotate about and in the same plane as anchor 102. When in operation, as previously described, each link member 104, 105, and 106 of the plurality of link members 103 can be inserted into a cardiac vein of the heart. First link member 104 can be configured, via joint 150a, to rotate about anchor 102 in a direction towards the mitral valve annulus (see the arrow denoted with A in FIG. 2A) to apply a force and/or pressure to the mitral valve annulus to change a geometry of the mitral valve annulus.

It follows that joint 150b can provide for movement (e.g. rotation) of second link member 105 relative to link member 104. In this regard, joint 150b can provide for link member 105 to rotate about and in the same plane as distal end 141 of first link member 104. Second link member 105 can be independently controlled by joint 150b relative to rotation of first link member 104 about anchor 102, via joint 150a, to rotate about distal end 141 of first link member 104 in a direction towards the mitral valve annulus (see the arrow denoted with B in FIG. 2A) to apply a force and/or pressure to the mitral valve annulus to change a geometry of the mitral valve annulus.

It follows still that third link member 106 can be rotatably coupled to second link member 105 by a joint 150c that provides for movement (e.g. rotation) of third link member 106 relative to second link member 105. Accordingly, third link member 106 can be independently controlled (as described below) relative to rotation of second link member 105 about distal end 141 of first link member 104.

In this manner, joints 150a, 150b and 150c provide for apparatus 100 to apply at least three forces and/or pressures to various positions on the mitral valve annulus. Further, joints 150a, 150b and 150c can also provide for each force and/or pressure applied to the mitral valve annulus to be capable of having a varying magnitude as these joints 150 can be used to position each of the link members 104, 105, and 106 at different angles to one another.

Each link member 104, 105, and 106 of the plurality of link members 103 can also be sized and shaped to inhibit pressure exerted on the left circumflex artery during rotation and/or actuated to apply a force and/or pressure to the mitral valve annulus to reduce backflow of blood through the mitral valve during normal heart operation. As noted above, the left circumflex artery lies in the left atrioventricular groove of the heart close to the mitral valve annulus. Each link member 104, 105, and 106 of the plurality of link members 103 can be sized and shaped such that one of the joints 150 lies adjacent to the left atrioventricular groove and the link members 103 do not exert pressure on the left circumflex artery. For example, in the example embodiments shown in the figures, apparatus 100 is configured such that joint 150c lies adjacent to the left atrioventricular groove. As previously described, joints 150 provide for independent rotation of each link member 104, 105, and 106 of the plurality of link members 103 about a distal end of an adjacent structure (e.g. an adjacent link member or anchor 102).

Figure 5:
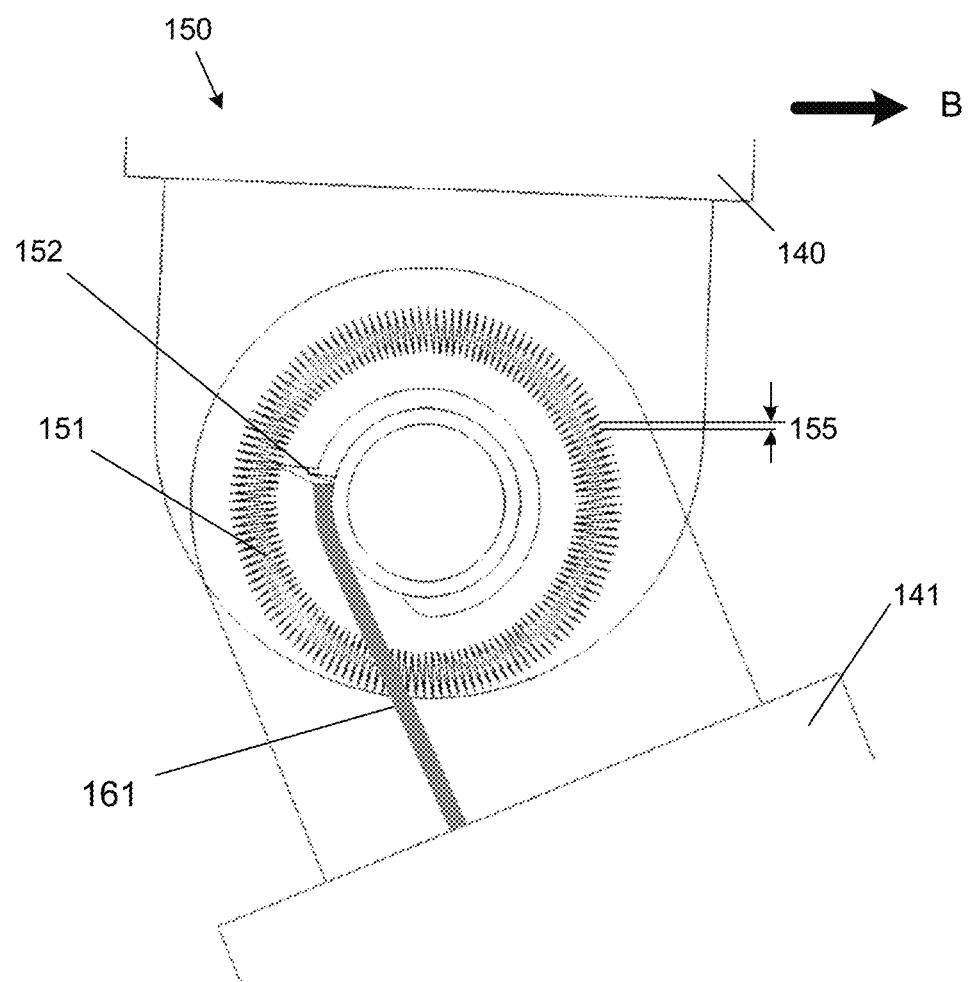
FIG. 5 is a top view of a joint of the apparatus of FIG. 2A, according to one example embodiment.

Referring to FIG. 5, a cross-sectional view of a joint 150 is provided. In the example embodiment shown therein, each joint 150 is a ratchet having a plurality of teeth 151 and a pawl 152. The pawl 152 of joint 150 is coupled to a tendon (described below) such that pulling the tendon disengages the pawl 152 from the teeth 151. When the pawl 152 is engaged with the teeth 151, the joint 150 can move only in one direction. Specifically, the angle of the teeth 151 and the pawl 152 can be configured such that the joint 150 can move in a direction to apply a force to the mitral annulus and not rotate in the opposite direction (e.g. away from the mitral annulus). Accordingly, the configuration of the teeth 151 and pawl 152 can inhibit the mitral annulus from rotating the link member in a direction away from the mitral annulus. When the pawl 152 is disengaged from the teeth 151 (e.g. by pulling the releasing tendon), the joint 150 can move in both directions. Accordingly, upon disengaging the pawl 152 from the teeth 151, proximal end 140 of one link member will rotate about distal end 141 of the adjacent link member in direction B (for example). In this respect, the amount of force and displacement placed on the mitral valve annulus by rotation of each link member 104, 105, 106 of the plurality of link members 103 can be controlled using actuation of the tendons.

The degree of control of the rotation of distal end 140 is directly proportionate to the distance 155 between each tooth of the plurality of teeth 151 in a joint 150. The distance 155 can vary depending on the diameter and length of the portion of the link members coupled to joint 150. In one example, the distance 155 space can be 0.1 mm.

Figure 6:
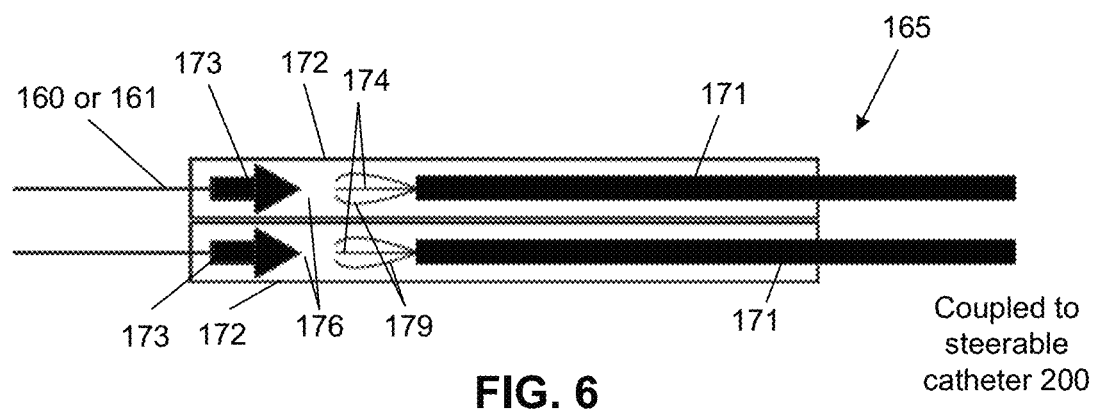
FIG. 6 is a side view showing an engagement mechanism between the tendons of the apparatus of FIG. 2A and a sub-catheter of a steerable catheter, according to one example embodiment.

In one embodiment, a user (e.g. a surgeon) can control movement (e.g. rotation) of each link member 104, 105 and 106 of the plurality of link members 103 using a steerable catheter 200. In one example embodiment, movement of each link member 104, 105 and 106 of the plurality of link members 103 can be provided by pulling and/or releasing respective actuating and releasing tendons 160, 161 using the steerable catheter 200. Specifically, the anchor 102 can engage a steerable catheter 200 via an engagement mechanism 165, which is schematically shown in FIG. 6. It should be noted that the engagement mechanism 165 shown in FIGS. 6-9B is one example of a mechanism for engaging the anchor 102 with the steerable catheter 200. Any appropriate mechanism for engaging the anchor 102 and the steerable catheter 200 can be used. Further, movement of the plurality of link members 103 can also be provided using other mechanisms.

Figure 11A:
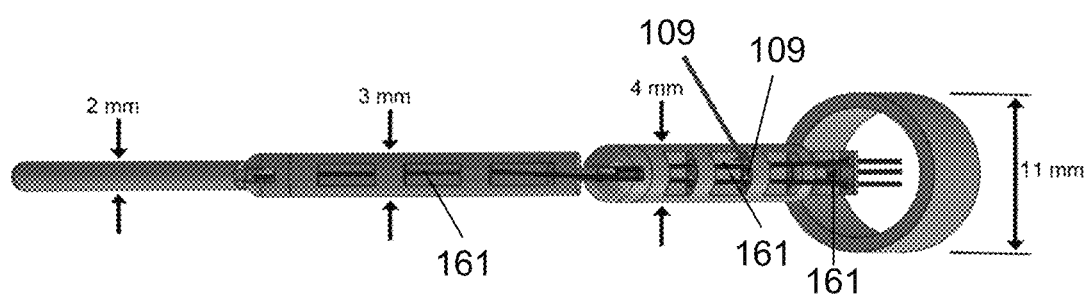
FIG. 11A is a posterior view of the apparatus of FIG. 10.

In the embodiments shown herein, each of the plurality of link members 103 (e.g. first link member 104, second link member 105 and third link member 106) is movably coupled to anchor 202 by actuating tendon 160 (see FIG. 11B) and release tendon 161 (see FIG. 11A). Each actuating tendon 160 is coupled to distal end 141 of each respective link member of the plurality of link members 103. Each release tendon 161 is coupled to a pawl 152 of joint 150 at proximal end 140 of the respective link member. As previously described, each actuating tendon 160 and release tendon 161 passes through the tendon supports 109 of each link member 104, 105 and 106 of the plurality of link members 103. Accordingly, the number of release tendons is equal to the number of link members and the number of actuating tendons is equal to the number of link members. Tendons 160, 161 can be made of any appropriate material having high tensile strength, such as but not limited to stainless steel or an alloy thereof. In one example, tendons 160, 161 can be made from product 304V by Fort Wayne Metals (Fort Wayne, Ind.).

In one example embodiment, referring to FIG. 6, each tendon (e.g. tendons 160, 161) of anchor 202 (shown in FIG. 8) can engage a sub-catheter 171 of a steerable catheter 200 via engagement mechanism 165. Engagement mechanism 165 includes a tendon (e.g. actuating tendon 160 or release tendon 161) having a tendon head 173, a sub-catheter 171 of steerable catheter 200 having a grabbing portion 174, and a tendon channel 172.

Sub-catheter 171 extends from steerable catheter 200 under the control of a user (e.g. a surgeon) in a direction towards tendons 160, 161 to engage with tendons 160, 161. The mechanism of sub-catheter 171 engaging a tendon is shown in FIG. 6 and described below.

Figure 8B:
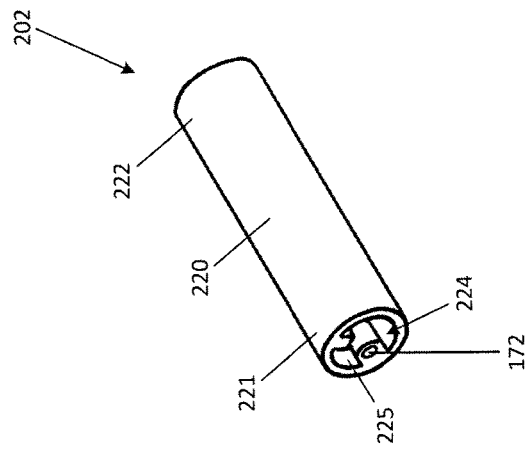
FIG. 8B is a perspective view of the anchor of FIG. 8A.
Figure 8A:
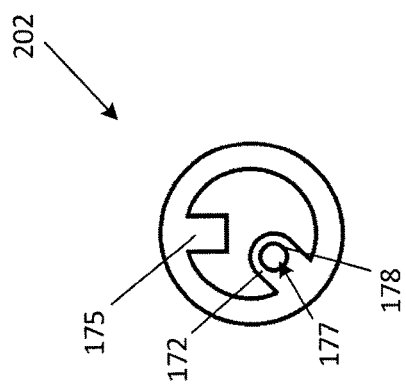
FIG. 8A is a cross-sectional view of the anchor of the apparatus of FIG. 2A, according to one example embodiment.

In the example embodiment shown in FIGS. 6, 8A and 8B, and referring only to actuating tendon 160 for ease of illustration, actuating tendon 160 having tendon head 173 is shown with tendon head 173 inserted into a tendon channel 172 of anchor 102. Tendon head 173 is sized and shaped to inhibit actuating tendon 160 from withdrawing from tendon channel 172. Sub-catheter 171 of steerable catheter 200 also inserts into tendon channel 172.

Tendon channel 172 includes a body 176 extending between first end 221 and second end 222 of anchor 202. Body 176 has an interior volume 177 defined by an inner channel wall 178. Interior volume 177 of tendon channel 172 is sized and shaped to provide for alignment of tendon head 173 and grabbing portion 174 of sub-catheter 171 when each of tendon head 173 and grabbing portion 174 are inserted into interior volume 177 of tendon channel 172. Tendon channel 172 can be integral with inner wall 225 of body 220. Tendon channel 172 extends within interior volume 224 of anchor 202 between first end 221 and second end 222.

Each tendon (e.g. actuating tendon 160 and release tendon 161) engages a separate sub-catheter 171 of steerable catheter 200 at an independent engagement mechanism 165 (e.g. within an independent tendon channel 172). Accordingly, each tendon (e.g. actuating tendon 160 and release tendon 161) of apparatus 100 can be independently actuated and/or released to independently control the movement (e.g. rotation) of a respective link member 104, 105 and 106 of the plurality of link members 103. Accordingly, the number of engagement mechanisms is the same as the total number of tendons.

For actuating and releasing tendons 160, 161, respectively, to control movement of a respective link member of the plurality of link members 103, grabbing portion 174 of sub-catheter 171 is used to engage tendon head 173. In the example embodiment shown in FIG. 6, tendon head 173 is schematically shown as being arrow-shaped and grabbing portion 174 of the sub-catheter 171 is sized and shaped to slide over tendon head 173 to engage tendon head 173. It will be appreciated that a tendon head 173 and/or a grabbing portion 174 having a differing shape and/or size beyond that shown in the figures may alternatively (or additionally) be provided, so long as the shapes of the tendon head 173 and the grabbing portion 174 are complementary (i.e. the grabbing portion 174 can engage and disengage the tendon head 173). The grabbing portion 174 of the sub-catheter 171 will get integrated with the arrow-shaped part of the tendon. The grabbing portion 174 can consist of several flexible pieces, such as tines or prongs 179, that can grab the tendon head 173 when the grabbing portion 174 is pushed towards tendon head 173. The grabbing portion 174 can be any flexible claw configuration appropriate for grabbing the tendon head 173.

Figure 7:
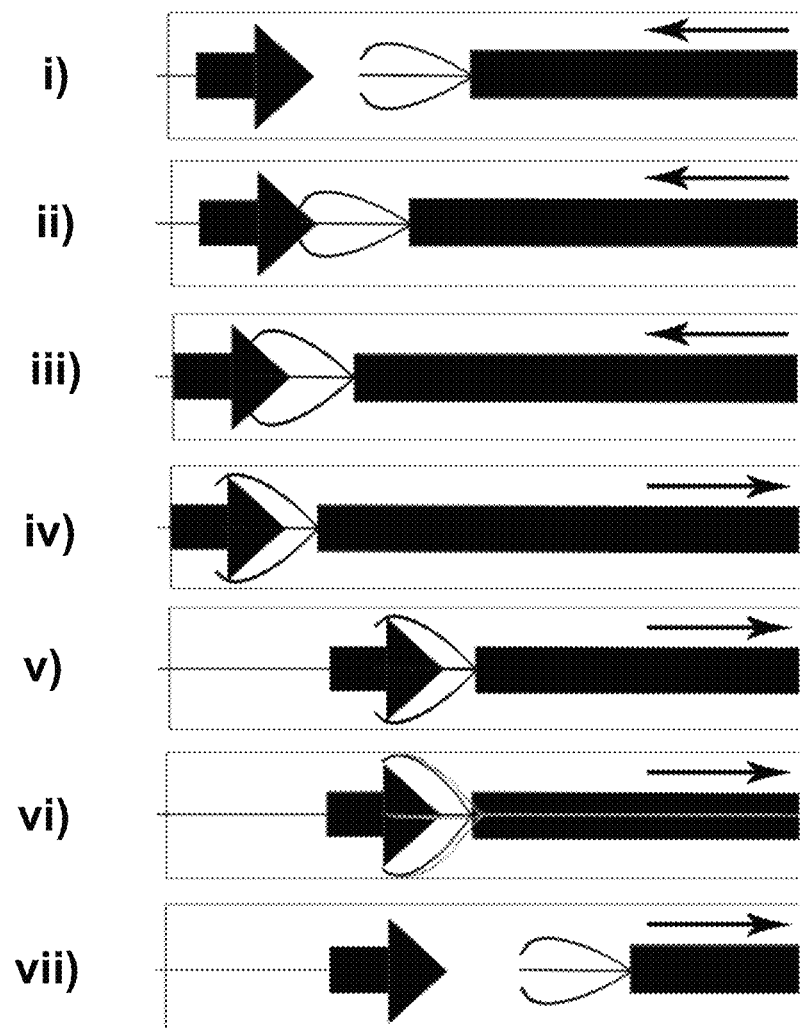
FIG. 7 is a schematic illustration depicting actuation and release of the sub-catheter of the engagement mechanism of FIG. 6, according to one example embodiment.

The steps for pulling and releasing a tendon by a sub-catheter 171 of a steerable catheter 200 are shown as steps i)-vii) of FIG. 7. Referring to step i), sub-catheter 171 is advanced in a direction towards tendon head 173 to engage tendon head 173. At step ii) grabbing portion 174 of sub-catheter 173 contacts tendon head 173. At step iii) each prong 179 of grabbing portion 174 begins to spread around tendon head 173 as grabbing portion 174 continues to advance towards tendon head 173 and begins to slide over tendon head 173. At step iv), grabbing portion 174 engages tendon head 173 and begins to travel in a direction away from tendon head 173. At step v), as grabbing portion 174 is engaged with tendon head 173, sub-catheter 171 moves away from tendon head 173 and tendon 160 is actuated. At step vi) grabbing portion 174 disengages tendon head 173.

At step vii), sub-catheter 171 continues to move away from tendon head 173 which remains stationary after being actuated.

FIGS. 8A and 8B show an example anchor 202 for aligning with a sub-catheter 171 of the steerable catheter 200. Tendon channel 172 and sub-catheter 171 can co-operate in a male/female relationship, where tendon channel 172 acts as a female part to receive sub-catheter 171 as a male part. To facilitate this co-operation, anchor 202 has a guiding rail 175 for co-operating with a guiding channel 190 of the steerable catheter 200. To align a tendon channel 172 of the anchor 202 with a sub-catheter 171 of steerable catheter 200, anchor 202 includes a guiding rail 175. The guiding rail 175 guides sub-catheter 171 of steerable catheter 200 towards tendon channel 172 for engaging a tendon head 173. Then, the engagement mechanism of FIG. 6 will be used to engage each sub-catheter with the related tendon in order to grab and pull the tendon.

Tendon channel 172 can be integrally formed with inner wall 225 defining an interior volume of anchor 202. Tendon channel 172 provides for receiving the tendon head 173 of tendons 160, 161 and is configured to inhibit movement of tendon head 173 out of the interior volume of anchor 202.

Figure 9B:
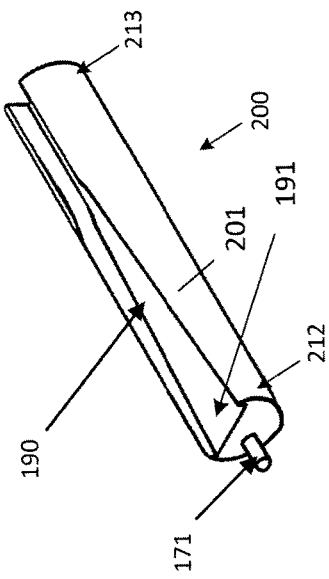
FIG. 9B is a perspective view the steerable catheter of FIG. 9A.
Figure 9A:
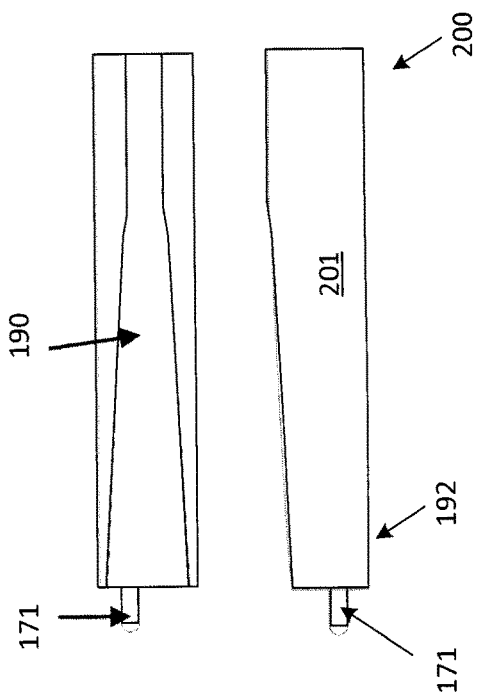
FIG. 9A shows a side view and a top view of the steerable catheter of the engagement mechanism of FIG. 6, according to one example embodiment.

Referring to FIGS. 8A, 9A and 9B, guiding rail 175 of anchor 202 is sized and shaped to receive a steerable catheter 200. In one example embodiment, steerable catheter 200 has a body 201 having a first end 212 and a second end 213. Sub-catheter 171 extends from first end 212 of steerable catheter 200 to be received at second end 222 of anchor 202. Guiding rail 175 is sized and shaped to mate with a guiding channel 190 of steerable catheter 200. Referring to FIG. 9B, guiding channel 190 can have an opening 191 at a proximal end 192 for mating with guiding rail 175. Mating of guiding rail 175 and guiding channel 190 can provide for alignment of sub-catheter 171 and a respective tendon channel 172, such that grabbing portion 174 of sub-catheter 171 of the steerable catheter 200 can be aligned with a respective tendon head 173 of tendon 160,161.

In one example embodiment, as shown in FIGS. 9A-9B, guiding channel 190 can be sized and shaped to engage the guiding rail 175 by slight rotation. For example, the guiding channel 190 can progressively narrow in width along a longitudinal length of the steerable catheter 200 to guide the guiding rail 175 of the anchor 202 to a narrow portion of guiding channel 190 distal to the proximal end of the steerable catheter 200. Rotation of the sub-catheter 171 as the guiding rail 175 enters the guiding channel 190, coupled with insertion of the steerable catheter 200 into the anchor 202, will provide for alignment of the sub-catheter 171 with a respective tendon channel 172 and consequently with a tendon 160, 161.

In one example embodiment of a method of inserting the apparatus 100, the apparatus 100 can be introduced into the coronary sinus using a sheath through the femoral vein by a surgeon. The joints 150 of apparatus 100 may be unlocked during the delivery method such that the link members 104, 105, 106 can move in more than one direction. This may provide for easier delivery of the apparatus 100 to the coronary sinus. When the anchor 102 is inserted into the coronary sinus ostium, the sheath through which the apparatus 100 is inserted may be retracted and anchor 102, which can for example be a self-expandable stent, can be deployed to fix (e.g. removably couple) the apparatus 100 in position inside of the coronary sinus. In one example, the anchor 102 can be compressed inside of the sheath during placement in the coronary sinus vein, and retracting the sheath can result in expansion of the anchor 102. Expansion of the anchor 102 can be stopped by the walls of the coronary sinus ostium. The force applied by anchor 102 to the walls of the coronary sinus ostium can maintain the apparatus 100 at a fixed position inside the coronary sinus.

For controlling the link members 104, 105, and 106 of the apparatus 100 after the apparatus 100 is fixed to the coronary sinus, the steerable catheter 200 can be introduced. The engagement mechanism 165 can provide for a surgeon to engage the steerable catheter 200 with the apparatus 100, and specifically to engage sub-catheter 171 with a tendon 160,161 of the anchor 102, by using translational movements of the steerable catheter 200. The grabbing portion 174 of the sub-catheter 171 can provide for the surgeon to control the position of each link member 104, 105, and 106 in order to apply certain forces to points/leaflets P1, P2 and P3 of the mitral valve annulus, for example. Tracking of the delivery sheath and steerable catheter 200 inside the patient body can be performed with using imaging methods such as X-ray imaging, for example.

It should be noted that apparatus 100 can be adjusted (i.e. the position of the link members 104, 105, and 106 can be independently manipulated to apply more than one force to the mitral valve annulus (e.g. to change the geometry of the mitral valve annulus) at various positions along the length of the coronary sinus vein) using steerable catheter 200 immediately after the apparatus 100 is positioned into the coronary sinus (e.g. during the same surgical procedure). Apparatus 100 can also be subsequently adjusted using steerable catheter 200 after being positioned into the coronary sinus (e.g. during a subsequent surgical procedure). For example, apparatus 100 may be adjusted by a surgeon using steerable catheter 200 if, for example, the geometry of the mitral valve naturally changes after the apparatus 100 was originally implanted into the coronary sinus ostium and mitral regurgitation through the mitral valve re-occurs. In this example, the force applied to the mitral valve annulus by the link members 104, 105, and 106 of apparatus 100 to change the geometry of the mitral valve can be re-adjusted after the apparatus 100 has been originally positioned into the coronary sinus by a surgeon re-inserting the steerable catheter 200 into the anchor 102 and manipulating the tendons 160,161 to re-position the link members 104, 105, and 106 as needed.

EXAMPLES

Figure 10:
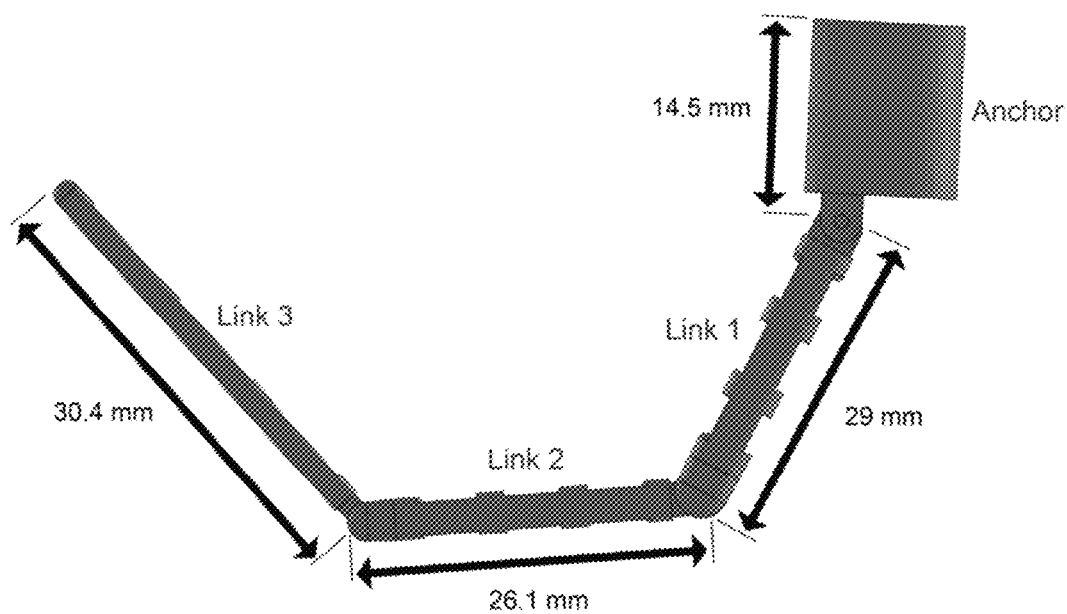
FIG. 10 is an atrial view of an apparatus for use in changing mitral valve annulus geometry, according to another example embodiment.

One specific example of a catheter-based apparatus for percutaneous treatment of mitral regurgitation is shown in FIG. 10. The apparatus shown therein includes three link members, (Link 1, Link 2 and Link 3, respectively) and an anchor. Link 1, Link 2 and Link 3 apply forces to the main three points P1, P2 and P3 of the mitral valve annulus, respectively. The lengths of Link 1, Link 2 and Link 3 are selected such that the location of the left circumflex artery is approximately placed close to the joint between Links 2 and 3 but is not directly compressed by these link members. In this manner, a surgeon may move the link members such that the amount of applied force on the left circumflex artery is minimized.

Figure 11B:
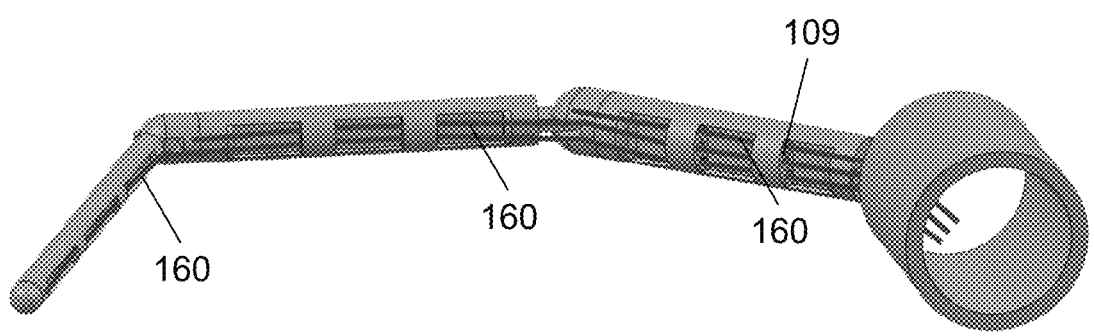
FIG. 11B is an anterior view of the apparatus of FIG. 10.

A posterior view of the apparatus of FIG. 10 is shown in FIG. 11A and an anterior view of the apparatus of FIG. 10 is shown in FIG. 11B. Link 1 has a diameter of 4 mm, Link 2 has a diameter of 3 mm and Link 3 has a diameter of 2 mm. Each diameter of each of Links 1, 2 and 3 is shown in FIG. 11. In this specific embodiment, the diameters of the links Link 1, Link 2 and Link 3 decrease from Link 1 to Link 3. The diameter of the coronary sinus also decreases along its length from the coronary ostium.

Determining the Length of Each Link

Figure 12B:
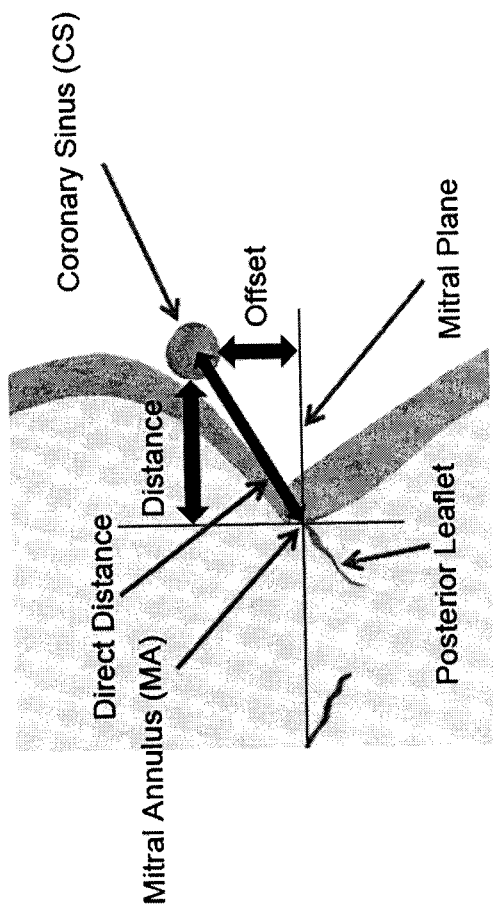
FIG. 12B shows an anterior cross sectional view of the mitral valve and coronary sinus depicting the location parameters of the coronary sinus with respect to the mitral annulus.
Figure 12A:
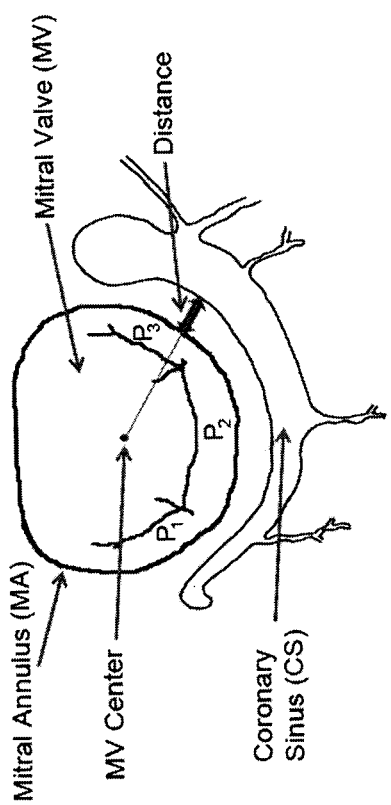
FIG. 12A shows an atrial view of the mitral valve and coronary sinus including the parameter of the distance from the coronary sinus to the mitral annulus.

FIG. 12A shows the atrial view of the mitral valve ("MV") and coronary sinus ("CS"). The parameter of the distance from CS to mitral annulus ("MA") is presented in this figure. FIG. 12B shows the anterior cross sectional view of the MV and CS. This figure depicts all the location parameters of CS with respect to MA.

The value of the offset from CS to MA was studied by D. Maselli et al. [1] at the two points P3 and P2. The reported values of this parameter were 9.7±3.2 mm and 5.7±3.3 mm at the points P2 and P3, respectively, which shows an increase of offset (from CS to MA) from the point P3 to the point P2.

The diameter of the CS was studied by R. del Valle-Fernandez et al. [2], and the pattern for this parameter was reported as a decreasing trend starting from CS ostium to the distal part of CS. The diameter of CS was also studied by S. El-Maasarany et al. [3] (5.6±1.6 mm for GCV size and 9.3±5.3 mm for CS size), A. Sorgente et al. [4] (11.78 mm for CS ostium diameter and 4.51 mm for GCV diameter), and D. Sahni et al. [5] (5.05±0.97 mm at CS ostium, 4.32±1.0 mm at middle and 2.88±0.58 mm at distal end of CS-GCV) which all show a decreasing profile of CS diameter starting from CS ostium to its distal end. The reported profile of the CS-GCV diameter by A. Chiribiri [6] also shows a decreasing pattern of this value starting from CS ostium to its distal end. S. Mao et al. [7] reported the diameter of CS only at CS ostium as 10.5±2.47 mm.

D. Valle-Fernandez et al. [2] reported the value of the direct distance from CS to MA along the CS at every 10 mm starting from CS ostium. The reported profile of the direct distance from CS to MA shows a maximum value at the middle point of the CS path. El-Maasarany et. al. [3] reported the direct distance from CS to MA starting from CS ostium with steps of 36*o*. The reported profile shows the maximum point in the second region (36*o*-72*o*) for 71.9% while for 28.1% of cases it is decreasing from CS ostium to the distal end of CS, continuously. The direct distance from CS to MA was reported by J. S. Shinbane et. al. [8] as 14.1±3.1 mm, 10.2±4.9 mm and 10.7±3.5 mm at 20, 40 and 60 mm from CS ostium, respectively.

The literature survey shows that the previous studies do not provide enough information on CS size and its geometry at the P points of the posterior leaflet. Hence, the size of CS and its location with respect to the MA were studied by the inventors by analyzing CT scan images. An important factor for the function of the catheter-based MR treatment devices is the offset from CS to MA. The reason is that if the CS has a big offset from MA, the apparatus cannot effectively push the posterior MA anteriorly to decrease the MR gap. Moreover, the dimensions of the catheter-based apparatus should be proper for the size of the CS.

In the study conducted by the inventors, CT scan data for 310 patients were investigated to extract the dimensions of CS and its location parameters with respect to MA. These patients underwent clinical assessment of presence or severity of coronary artery diseases at St. Michael's Hospital of Toronto. Out of the 310 patients, 204 of them had adequate properties for further analysis (74 females and 130 males, age 62±11). The rest did not have enough resolution, or some parts of the CS or the MA were not captured in the images. The clinical characteristics of the study population are listed in Table 1.

TABLE 1

Clinical characteristics of study population

| Characteristics | Value |
| --- | --- |
| Age, year, mean ± SD | 62 ± 11 |
| Gender, M/F | 130/74 |
| Wight, kg, mean ± SD | 87.0 ± 17.8 |
| Height, cm, mean ± SD | 175.1 ± 11.2 |
| BSA, m², mean ± SD | 2.0 ± 0.3 |
| Degree of MR | |
| 0 | 159 (78%) |
| 1+ | 38 (19%) |
| 2+ | 7 (3%) |
| 3+ | 0 |
| 4+ | 0 |
| LAVI, ml/m2, mean ± SD | 35.1 ± 9.8 |
| LVMI, g/m2, mean ± SD | 86.3 ± 20.0 |
| LVEF, %, mean ± SD | 53.7 ± 5.4 |
| Left Ventricular Diastole Size (Diameter), cm, mean ± SD | 4.9 ± 0.6 |
| Left Ventricular Systole Size (Diameter), cm, mean ± SD | 3.2 ± 0.6 |

Dimension and location parameters of CS that were measured are diameter of CS, offset of CS from MA, and distance and direct distance from CS to MA. All measurements were performed at 75% of the RR interval. Measurements were performed at the three points of P1, P2 and P3 (i.e. the P points). These three points on the MA are related to three scallops (P1, P2 and P3) of the posterior leaflet. The point P2 is located approximately in the middle of the P2 scallop. The angle between connecting lines from MV center to the point P2 and point P1 is around 60°; the angle between connecting lines from MV center to the point P2 and the point P3 is also around 60° [9].

Figure 13:
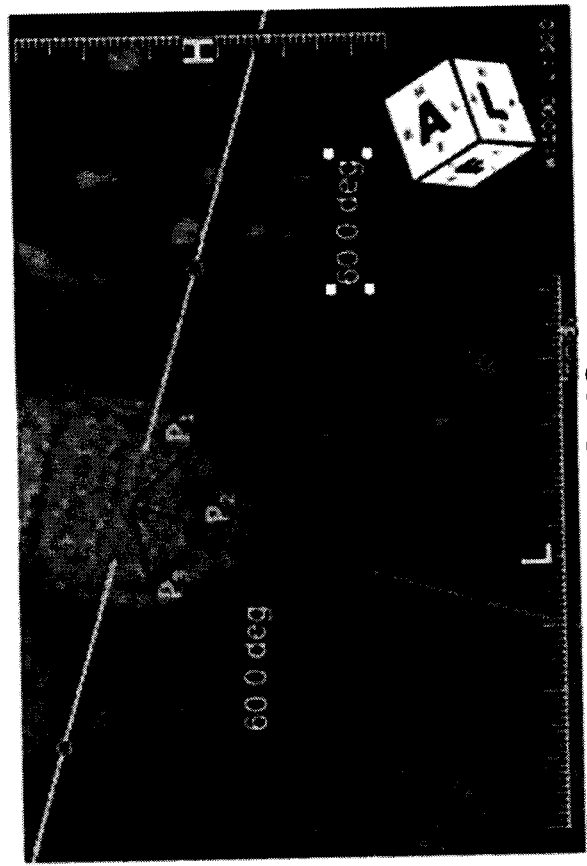
FIG. 13 is a computerized tomography (CT) scan showing three lines connecting the mitral valve center to the points P1, P2 and P3 (shown on FIG. 12A).

For all of the measurements, the three points of P1, P2 and P3 were found and considered for measurement of CS size and location. FIG. 13 depicts the three lines connecting the MV center to the points P1, P2 and P3 in a sample CT scan image. Measurements of CS parameters are performed at these three points by aligning a view plane on the respective connecting lines. For instance, FIG. 14A shows the measurement of CS diameter at the point P3 which is 8.39 mm in this example. The measurements of CS offset and distance from MA are performed with the same method. FIG. 14B shows an example measurement of CS offset from MA at the point P2 which is 3.39 mm.

In this study, the extracted continuous data are presented as mean values±Standard Deviation (SD) while the categorical data are provided as percentages and frequencies. IBM SPSS Statistics software (version 23, IBM Inc., New York) was used for performing all statistical analyses. The student's t-test was performed to find the difference between two sets of data. For finding the difference between three or more sets of data, the 1-way ANOVA test was performed. For these analyses, a p-value<0.05 was considered statistically significant. The correlations (R values) in this study were computed with linear regression analysis. The results of the study are now discussed.

The diameter of the CS was found to be 4.9±1.3 mm, 6.7±1.6 mm and 9.37±2.0 at points P1, P2 and P3, respectively. The diagram of the CS diameter at these three points is shown in FIG. 15A. As shown in this figure, there is a significant decrease in diameter along the CS from point P3 to P1 (P<0.001).

Figure 16:
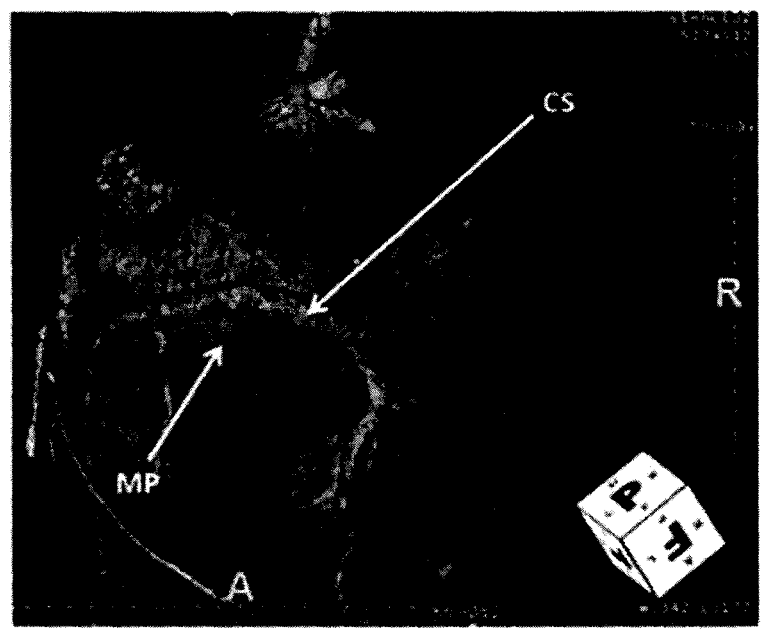
FIG. 16 is a 3D image of a heart generated from CT scan data.

The offset of the CS from the MA was found to be 4.7±2.6 mm, 8.8±3.4 mm and 5.4±3.3 mm at points P1, P2 and P3, respectively. FIG. 15B shows that this offset is maximum at the point P2 among the three points (P<0.001). In FIG. 16, the 3D generated image of a heart from CT scan data shows that the CS does not lie on the mitral plane and there is an offset from CS to MA.

Figure 17A:
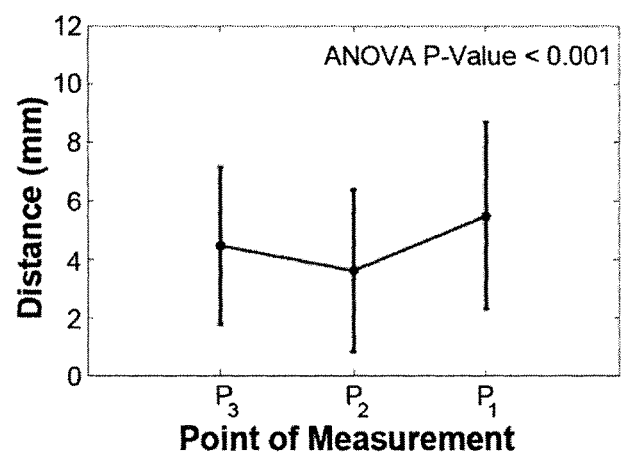
FIG. 17A is a graph showing distances from the coronary sinus to the mitral annulus from each of points P1, P2 and P3.
Figure 17B:
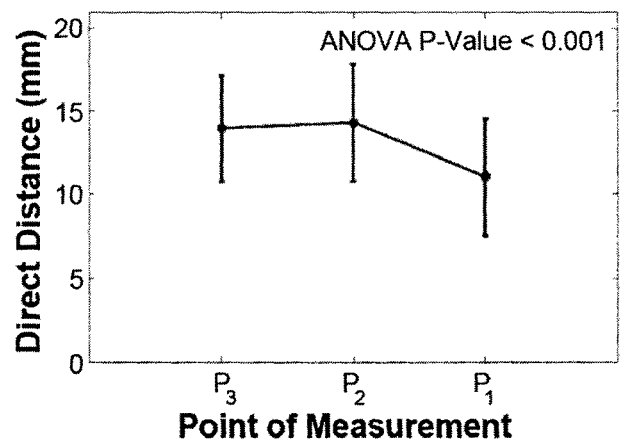
FIG. 17B is another graph showing direct distances from the coronary sinus to the mitral annulus from each of points P1, P2 and P3.

The distance from CS to MA was found to be 5.5±3.2 mm, 3.6±2.8 mm and 4.5±2.7 mm at points P1, P2 and P3, respectively. The direct distance from CS to MA was found to be 11.0±3.5 mm, 14.3±3.5 mm and 13.9±3.2 mm at points P1, P2 and P3, respectively. FIGS. 17A and 17B depict the profiles for these two values from points P3 to P1.

The angle between the lines crossing from the center of the MV and the points P1, P2 and P3 is approximately 60° [9]. The radius of MA is approximately 15.5 mm [10]. It is noteworthy to mention that the diameter of MA varies during the cardiac cycle [2]. Here, the mean value of the measured radius in the end-systole and end-diastole has been selected with considering both genders of male and female.

The total length of CS-GCV which is almost on the mitral plane is reported as 120 mm, approximately [2, 4, 11, 12]. The distance from CS ostium to the cross point between CS-GCV and LCx is reported as 79 mm, approximately [6, 13].

The distance from the projection of the CS ostium on the MA to the posterior commissure point is approximately 3.6 mm. This value was calculated from two measured distances: the distance from the projection of the CS ostium to the right fibrous trigone which is 15.2 mm, and the distance from posterior commissure point to the right fibrous trigone which is 11.6 mm [14].

The distance from the posterior commissure point to the anterior commissure point on the MA is 62.2 mm [14]. Thus, the distance from the posterior commissure point to the point P2 on the MA is 31.1 mm. Using these values, the distance from the projection of CS ostium to the P2 point on the MA was calculated as 27.5 mm (31.1−3.6=27.5 mm).

Using the MA radius (15.5 mm) and the distance from coronary sinus ostium to P2 point (27.5 mm), the angle from the coronary sinus ostium to the point P2 (with the center of mitral valve center) was calculated as 101.6°. The angle from point P3 to point P2 was 60°. Thus, the angle (θ) from coronary sinus ostium to the point P3 was 41.6° (101.6−60=41.6).

Figure 18:
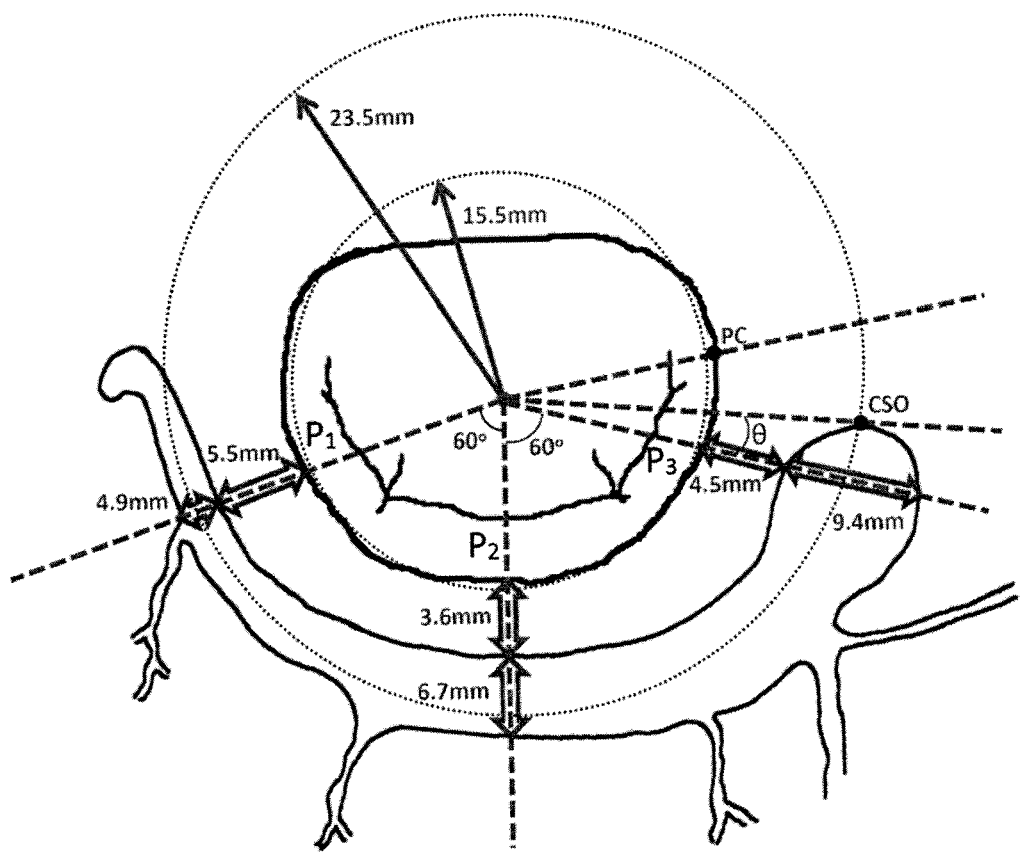
FIG. 18 is an atrial top view of the Mitral Valve (MV) and the Coronary Sinus (CS) with geometrical parameters calculated as per the examples provided.

FIG. 18 shows the MV and the CS from an atrial top view with the geometrical parameters. The diameter of CS and its distance from the MA at points P1, P2 and P3 were extracted from the performed CT scan image analysis.

Figure 19:
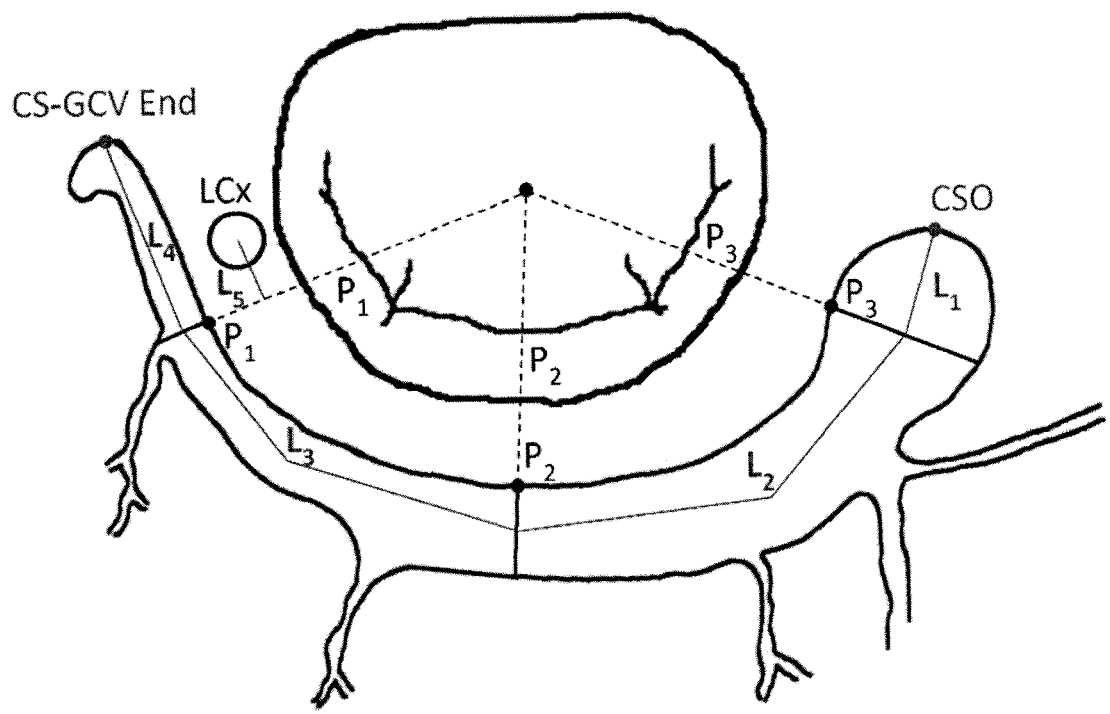
FIG. 19 is an atrial top view of the mitral valve and the coronary sinus showing different lengths in the geometry of CS and MV.

From the calculations above, the length from the CS ostium to the point P3 on the CS path (L1) is 17 mm, approximately. The length from the point P3 to the point P2 (L2) and from the point P2 to the point P1 (L3), both were 24.6 mm, approximately. With considering the total length of the CS which is 120 mm, the distance from the point P1 to the end of the CS-GCV (L4) was approximately 53.8 mm. The distance from the point P1 to the cross point between CS-GCV and LCx (L5) was calculated as 12.8 mm. These lengths are shown in FIG. 19.

It is noteworthy to mention that these calculated lengths are considered in the middle path of the coronary sinus. However, the apparatus 100 will push the mitral annulus from the inner path of the coronary sinus (closer to the posterior leaflet of mitral valve). Therefore, the sizes of the links for the apparatus 100 may be relatively smaller than these calculated lengths.

Determining the Number of Teeth in Each Joint

Figure 20:
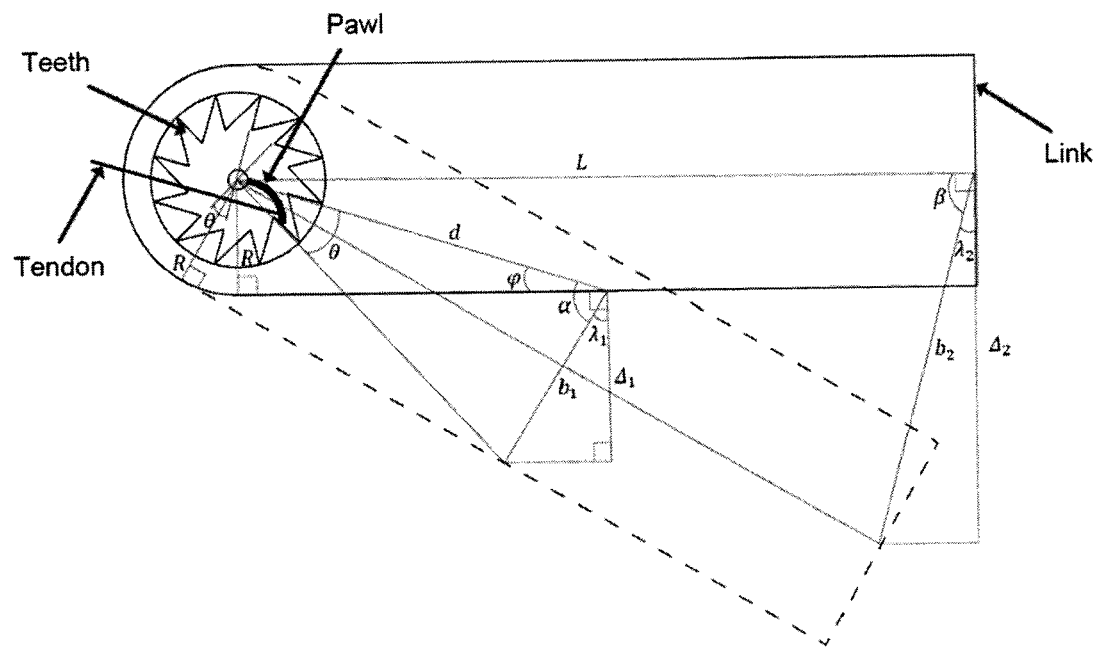
FIG. 20 is a cross-sectional view of a joint of the apparatus of FIG. 2A, according to one embodiment, showing geometrical references for calculations to determine displacements due to the rotation of the link in the middle and the tip of the link, respectively.

Another parameter in designing the one-directional joint is the number of teeth. The following calculations were performed to find the proper number of teeth for each joint of the apparatus 100. These geometrical calculations are considered based on FIG. 20. As shown in FIG. 20, Δ1 and Δ2 are the generated displacements due to the rotation of the link in the middle and the tip of a given link, respectively. The displacement of Δ1 is generated in the position of the P points. Equations 7 and 12 can be used to find the values of Δ1 and Δ2, respectively. In these equations, θ is the angle between two adjacent teeth of the ratchet joint; and R and L are the radius and length of the link, respectively.

$$R^2 + \left(\frac{L}{2}\right)^2 = d^2 \rightarrow d = \sqrt{R^2 + \frac{L^2}{4}} \quad (1)$$

$$b_1 = 2d\sin\left(\frac{\theta}{2}\right) \quad (2)$$

$$\alpha = 90 - \frac{\theta}{2} \quad (3)$$

$$\varphi = \tan^{-1}\left(\frac{2R}{L}\right) \quad (4)$$

$$\lambda_1 = 90 - (\alpha - \varphi) = 90 + \varphi - \alpha \quad (5)$$

$$\Delta_1 = b_1\cos(\lambda_1) = \quad (6)$$

$$2d\sin\left(\frac{\theta}{2}\right)\cos\lambda_1 = 2\left(\sqrt{R^2 + \frac{L^2}{4}}\right)\sin\left(\frac{\theta}{2}\right)\cos(90 + \varphi - \alpha) =$$

$$2\left(\sqrt{R^2 + \frac{L^2}{4}}\right)\sin\left(\frac{\theta}{2}\right)\cos\left(90 + \tan^{-1}\frac{2R}{L} - 90 + \frac{\theta}{2}\right) =$$

$$2\left(\sqrt{R^2 + \frac{L^2}{4}}\right)\sin\left(\frac{\theta}{2}\right)\cos\left(\tan^{-1}\left(\frac{2R}{L}\right) + \frac{\theta}{2}\right)$$

$$\Delta_1 = 2\left(\sqrt{R^2 + \frac{L^2}{4}}\right)\sin\left(\frac{\theta}{2}\right)\cos\left(\tan^{-1}\left(\frac{2R}{L}\right) + \frac{\theta}{2}\right) \quad (7)$$

$$b_2 = 2L\sin\left(\frac{\theta}{2}\right) \quad (8)$$

$$\beta = 90 - \frac{\theta}{2} \quad (9)$$

$$\lambda_2 = 90 - \beta = 90 - \left(90 - \frac{\theta}{2}\right) = \frac{\theta}{2} \quad (10)$$

$$\Delta_2 = b_2\cos(\lambda_2) = b_2\cos\left(\frac{\theta}{2}\right) = 2L\sin\left(\frac{\theta}{2}\right)\cos\left(\frac{\theta}{2}\right) \quad (11)$$

$$\Delta_2 = 2L\sin\left(\frac{\theta}{2}\right)\cos\left(\frac{\theta}{2}\right) \quad (12)$$

Increasing the number of teeth results in higher resolution in the generated displacement. However, there are two main constraints in the maximum number of teeth that may be considered in the design. The first limitation is related to the smallest feature that can be fabricated. This factor depends on the fabrication method and material. Some fabrication companies provide ultra-high resolution for 3D printing of the designs with polymer materials (resolution of around 10 μm) [15]. However, experience shows that usually a minimum feature size of at least three times more than the claimed number by the companies should be considered in the design procedure. If the design includes channels with a high aspect ratio, there is a problem of cleaning the channels from waste material. This problem can be solved by making the length of channels in the design as short as possible. This can be seen in the design of the apparatus 100 where gaps are considered in the links to decrease the aspect ratio of the tendon supports. Moreover, the minimum feature size and gap in the design of the example implementation of apparatus 100 are above 100 μm and above 50 μm, respectively. Therefore, fabrication of the apparatus 100 using high resolution 3D printing technologies is feasible.

Table 2 provides the generated displacement for each link considering the angle of 5 degrees between two adjacent teeth of the ratchet joint.

TABLE 2

Generated Displacement by the Links of the Apparatus

|  | R (mm) | L (mm) | θ (mm) | Δ1 (mm) |
|---|---|---|---|---|
| Link 1 | 2 | 29 | 5 | 1.2 |
| Link 2 | 1.5 | 26.1 | 5 | 1.1 |
| Link 3 | 1 | 30.4 | 5 | 1.3 |

FEM Simulation of the Apparatus Under Applied Force

To determine the amount of force applied by each link member to the mitral valve annulus (MA), FEM simulation was performed on all three link members of the apparatus. The fabrication material considered was VisiJet EX200. VisiJet EX200 is a bio-compatible material that has passed the USP Class VI tests. Accordingly, this material can be used in surgical instruments and medical apparatuses which are in direct contact with the human body. The properties of this material are given in Table 1. FEM simulations were performed using COMSOL Multiphysics (COMSOL, Stockholm, Sweden).

Figure 21:
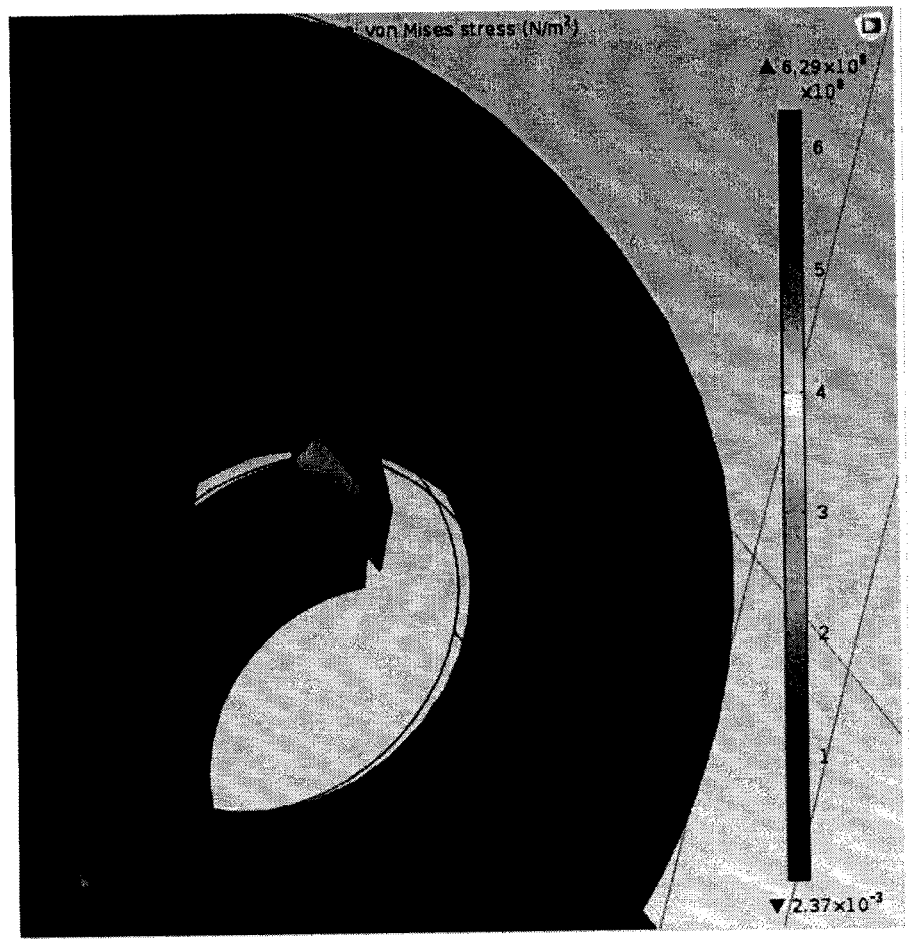
FIG. 21 is a graph showing the generated stress on a one-directional joint of the apparatus of FIG. 2A while the first member applies a 0.7 N force, according to one example.

The results show that the most vulnerable part of the apparatus under the applied force is the locking mechanism. FIG. 21 shows the generated stress on the Paw of the one-directional joint while Link 1 applies the force of 0.7 N (that is twice of the maximum applied force which is around 0.35 N).

TABLE 3

VisiJet EX200 Material Properties

| Property | Value |
|---|---|
| Density | 1.02 g/cm³ |
| Tensile Strength | 42.4 MPa |
| Tensile Modulus | 1463 MPa |
| Heat Distortion Temperature at 0.45 MPa | 56° C. |
| Poisson's Ratio | 0.42 |

This result shows that the maximum generated stress, which is around 629 MPa, is much higher than the ultimate tensile strength of the material (42.4 MPa). Based on this analysis, this part of the apparatus cannot be fabricated from the polymer material with such properties. Another option for the material used to make the apparatus is Titanium alloy (Ti-6Al-4V) which has an ultimate tensile strength of 965 MPa. Titanium alloy is a bio-compatible material and can be used in the fabrication of implantable devices. Simulations showed that the generated stress in Link 2 and Link 3 are 322 MPa and 218 MPa, respectively, when Titanium alloy is used. Therefore, the apparatus can be fabricated from Titanium alloy.

The amount of force applied by the apparatus to the MA should be determined for being in a proper range. A low amount of applied force will be ineffective for improving MR grade. On the other hand, an excessive amount of applied force can hurt or even puncture the heart tissue. In order to avoid such incident and to have a proper amount of the applied force, the proper range of the force that can be applied to the MA from the CS should be extracted. Furthermore, the amount of movement generated in the MA due to the applied force needs to be found. Another reason for extracting the value of the required force is the evaluation of the apparatus strength under the applied force using FEM simulations. The current subsection explains the experiment that was performed for measuring the required force applied to the MA.

For performing the experiments, a pig heart was used because its structure, dimensions and function are similar to the human heart [16]. The pig heart was suspended inside of a bucket of NaCl by using a stand during the experiment. Several sutures were utilized to suspend the heart from the stand. The temperature of the solution was set to 37° C. which is the usual temperature of the human body. A thermo circulating heater (Thermo Haake DC10) with a heating range of 25° C. to 100° C. was used for this purpose.

For temperature reading of the saline solution of NaCl, an Omegaette thermometer was utilized in this experiment. The resolution of this thermometer is 0.1° C. and its accuracy is ±1° C. The range of temperature sensing for this thermometer is −200° C. to 1370° C. The wire thermocouple of this thermometer was inserted into the bucket of NaCl solution to read the temperature of the solution. Based on the number which was shown by the thermometer, the temperature of the solution was 33.8° C. This difference between the set temperature of the thermo circulating heater and the thermometer was because of the thermal loss from the heating source inside the thermos circulating heater to the heating element which was immersed in the NaCl solution. For increasing the temperature of the solution to almost 37° C., the thermal circulator was set to 39.8° C.

Figure 22A:
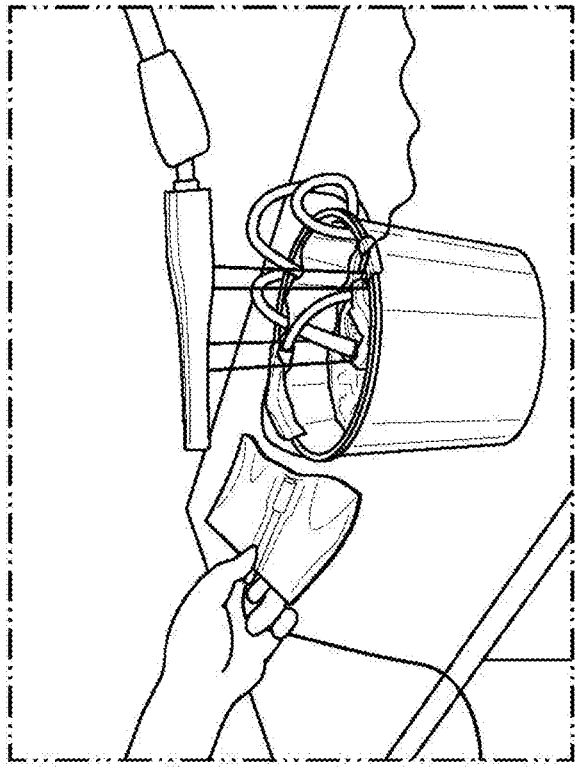
FIG. 22A is an image showing an experimental setup for measuring the applied force to the mitral annulus from the coronary sinus, according to one example embodiment.
Figure 22B:
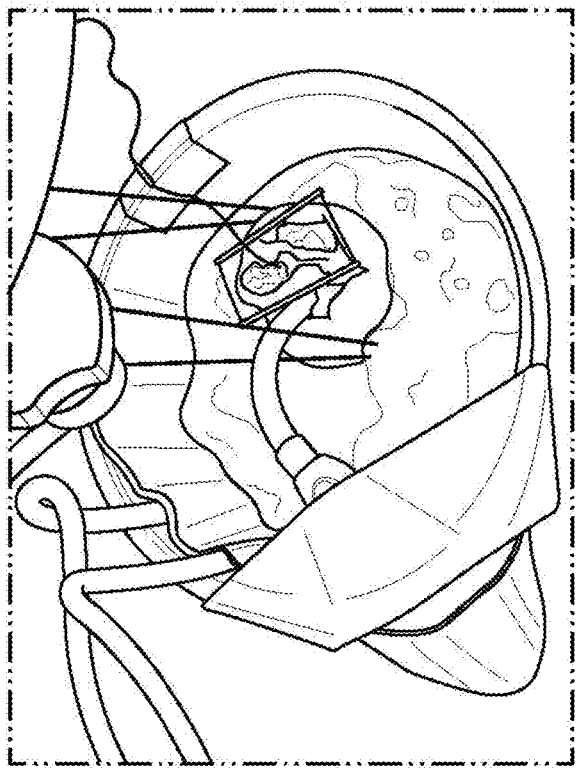
FIG. 22B is another image of the experimental setup for measuring the applied force to the mitral annulus from the coronary sinus, according to one example embodiment.

For measuring the amount of displacement of the MA, a transparent ruler with a 500 μm indicator was attached to the top of the pig heart with using a screw. The screw was inserted into the pig heart to keep the ruler exactly on the pig heart and on the MA to measure its displacement when force was applied. An ATI Nano-17 force sensor with a measurement resolution of 0.003 N was used to measure the force which was applied to the MA from the CS location. For reading the displacement from the ruler, which was attached to the pig heart, a desk magnifier with a 7× magnification was used. A pump was used to pour the NaCl solution on the pig heart, so the portion of the pig heart which was outside of the NaCl was kept fresh during the experiment. FIGS. 22A and 22B show different parts of the total experimental setup.

The results of the experiment are presented in Table 4.

TABLE 4

| | Applied Force for Generating Displacements at P1, P2 and P3 | | |
|---|---|---|---|
| Displacement | 1 mm | 2 mm | 3 mm |
| Applied force at P1 | 0.075 ± 0.009N | 0.178 ± 0.011N | 0.298 ± 0.298N |
| Applied force at P2 | 0.056 ± 0.013N | 0.103 ± 0.014N | 0.197 ± 0.016N |
| Applied force at P3 | 0.080 ± 0.011N | 0.177 ± 0.017N | 0.327 ± 0.019N |

The results obtained in this study for the amount of force applied to the P2 point is in agreement with the results reported by M. O. Jensen et al [17]. They showed in their study that the dynamic force applied to an annuloplasty ring at posterior point of the ring (P2 point of MA) is less than 0.4 N. The results of the study performed by the inventors show that the applied force to the mitral annulus for generating 3 mm of displacement (which is reasonable amount of displacement to improve MR grade significantly) is less than 0.35 N.

CFD Simulation of Blood Inside CS

Implanting the designed apparatus inside the coronary sinus (CS) will cause blood flow turbulence. Consequently, thrombosis (formation of blood clots) may occur inside the CS causing fatal problems. To make sure that the apparatus is safe to be implanted inside the CS from the aspect of blood flow, CFD simulation was performed using COMSOL Multiphysics. The 3D model of the CS was developed in SolidWorks software using the geometrical parameters extracted from the CT scan analysis. The developed 3D model of the CS was imported to COMSOL software for CFD simulation. Blood in the CS at normal physiological conditions was considered to be a Newtonian liquid with a constant dynamic viscosity of 3.5 cP (0.0035 Pa·s). The considered blood pressure inside the CS was around 10 mmHg (1300 Pa). The mean value of the blood flow in the CS was 123 ml/min. Using this value and the diameter of the CS, the velocity of blood flow in the CS ostium was calculated as 0.0225 m/s which was set as the boundary condition in the simulation.

Figure 23A:
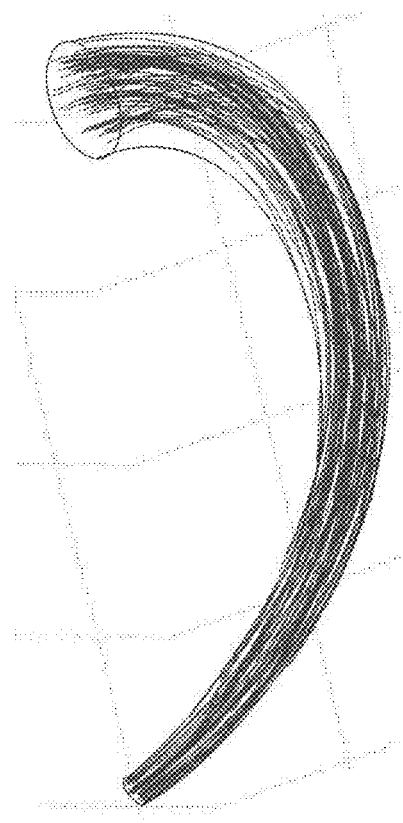
FIG. 23A is a computational fluid dynamics schematic illustration depicting blood flow streamlines in the coronary sinus without the apparatus of FIG. 2A.
Figure 23B:
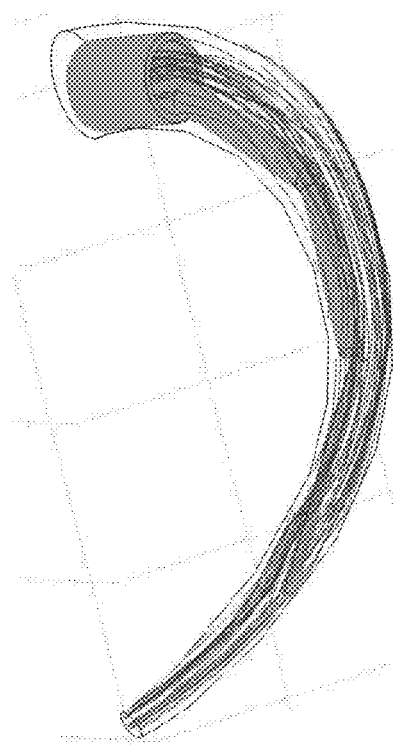
FIG. 23B is a computational fluid dynamics schematic illustration depicting blood flow streamlines in the coronary sinus with the implanted apparatus of FIG. 2A.
Figure 24B:
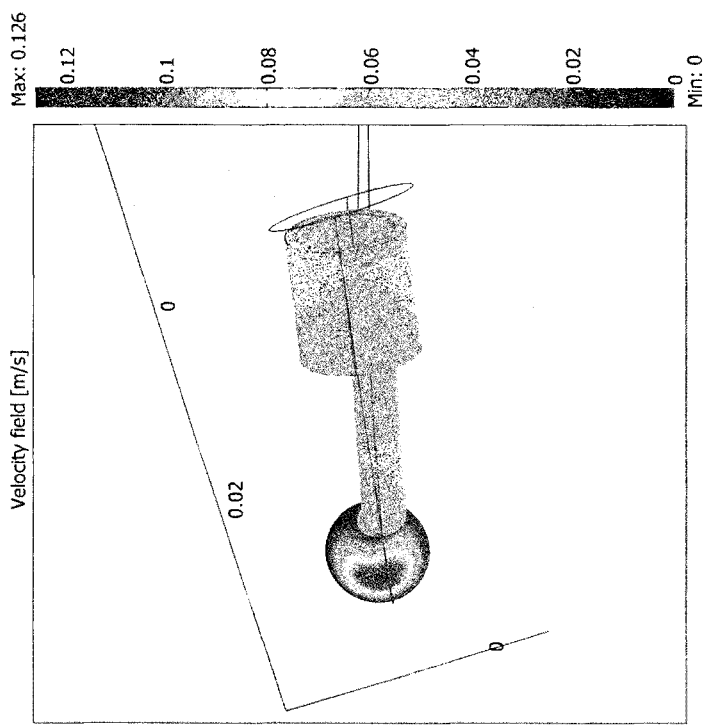
FIG. 24B is a computational fluid dynamics schematic illustration showing a velocity field of blood flow at P2 in the coronary sinus with the implanted apparatus of FIG. 2A.
Figure 24A:
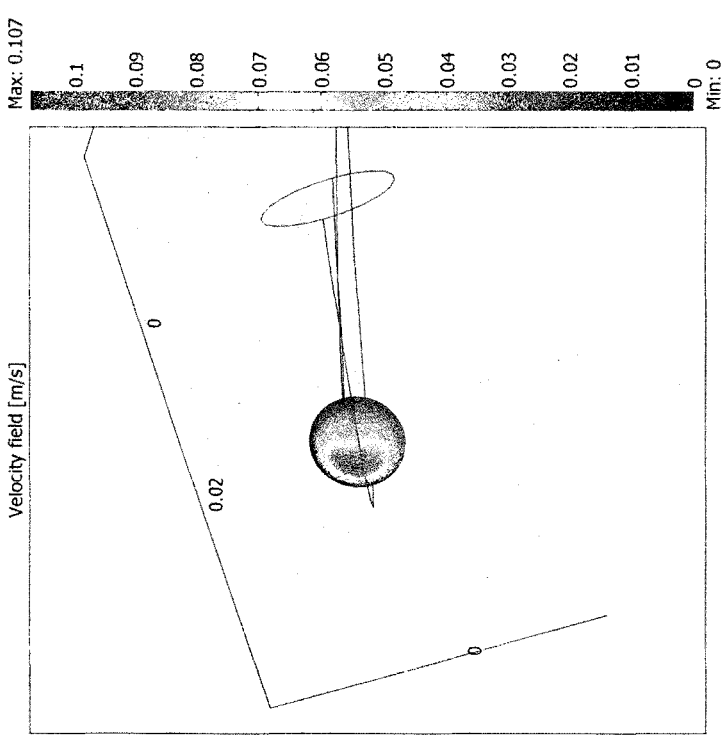
FIG. 24A is a computational fluid dynamics schematic illustration showing a velocity field of blood flow at P2 in the coronary sinus without the implanted apparatus of FIG. 2A.

FIGS. 23A and 23B show the simulation results of blood flow streamlines in the CS with the implanted apparatus and without the implanted apparatus, respectively. FIGS. 24A and 24B depict the velocity field of blood flow at the P2 point for these two different scenarios. The simulation results showed that with implantation of the apparatus inside the CS, the blood flow rate decreases to 116.8 mL/min which is still within the normal range of blood flow rate inside the CS. Therefore, installation of the apparatus inside the CS does not cause CS stenosis.

The simulation results also showed that the maximum Reynolds number when the apparatus was located inside the CS was 264.4. The threshold of the Reynolds number for the blood flow to be a turbulent flow is 2000. Therefore, implanting the apparatus inside the CS is safe in terms of not causing thrombosis.

While the above description describes features of example embodiments, it will be appreciated that some features and/or functions of the described embodiments are susceptible to modification without departing from the spirit and principles of operation of the described embodiments. For example, the various characteristics which are described by means of the represented embodiments or examples may be selectively combined with each other. Accordingly, what has been described above is intended to be illustrative of the claimed concept and non-limiting. It will be understood by persons skilled in the art that other variants and modifications may be made without departing from the scope of the teachings herein as defined in the claims appended hereto. The scope of the claims should not be limited by the preferred embodiments and examples, but should be given the broadest interpretation consistent with the description as a whole.

REFERENCES

[1] D. Maselli, F. Guarracino, F. Chiaramonti, F. Mangia, G. Borelli, and G. Minzioni, "Percutaneous mitral annuloplasty an anatomic study of human coronary sinus and its relation with mitral valve annulus and coronary arteries," Circulation, vol. 114, no. 5, pp. 377-380, 2006.

[2] R. del Valle-Fernandez, V. Jelnin, G. Panagopoulos, and C. E. Ruiz, "Insight into the dynamics of the coronary sinus/great cardiac vein and the mitral annulus implications for percutaneous mitral annuloplasty techniques," Circulation: Cardiovascular Interventions, vol. 2, no. 6, pp. 557-564, 2009.

[3] S. El-Maasarany, C. G. Ferrett, A. Firth, M. Sheppard, and M. Y. Henein, "The coronary sinus conduit function: anatomical study (relationship to adjacent structures)," Europace, vol. 7, no. 5, pp. 475-481, 2005.

[4] A. Sorgente, Q. A. Truong, C. Conca, J. P. Singh, U. Hoffmann, F. F. Faletra, C. Klersy, R. Bhatia, G. B. Pedrazzini, E. Pasotti et al., "Influence of left atrial and ventricular volumes on the relation between mitral valve annulus and coronary sinus," The American Journal of Cardiology, vol. 102, no. 7, pp. 890-896, 2008.

[5] D. Sahni, A. Randhawa, A. Aggarwal, and M. K. Rohit, "Spatial relationship of coronary sinus-great cardiac vein with adjoining anatomic structures: a key element in predicting the success of percutaneous transvenous mitral annuloplasty." The Journal of Heart Valve Disease, vol. 23, no. 2, pp. 184-192, 2014.

[6] A. Chiribiri, S. Kelle, U. Köhler, L. F. Tops, B. Schnackenburg, R. Bonamini, J. J. Bax, E. Fleck, and E. Nagel, "Magnetic resonance cardiac vein imaging: relation to mitral valve annulus and left circumflex coronary artery," JACC: Cardiovascular Imaging, vol. 1, no. 6, pp. 729-738, 2008.

[7] S. Mao, J. S. Shinbane, M. J. Girsky, J. Child, S. Carson, R. J. Oudiz, and M. J. Budoff, "Coronary venous imaging with electron beam computed tomographic angiography: three-dimensional mapping and relationship with coronary arteries," American Heart Journal, vol. 150, no. 2, pp. 315-322, 2005.

[8] J. S. Shinbane, M. D. Lesh, W. G. Stevenson, T. S. Klitzner, P. D. Natterson, I. Wiener, P. C. Ursell, and L. A. Saxon, "Anatomic and electrophysiologic relation between the coronary sinus and mitral annulus: implications for ablation of left-sided accessory pathways," American Heart Journal, vol. 135, no. 1, pp. 93-98, 1998.

[9] P. Lancellotti, L. Moura, L. A. Pierard, B. A. Popescu, C. Tribouilloy, A. Hagendorff, J.-L. Monin, L. Badano, J. L. Zamorano, R. Sicari et al., "European association of echocardiography recommendations for the assessment of valvular regurgitation. part 2: mitral and tricuspid regurgitation (native valve disease)," European Heart Journal-Cardiovascular Imaging, vol. 11, no. 4, pp. 307-332, 2010.

[10] G. Dwivedi, G. Mahadevan, D. Jimenez, M. Frenneaux, and R. P. Steeds, "Reference values for mitral and tricuspid annular dimensions using two-dimensional echocardiography," Journal of Echo Research and Practice, vol. 1, no. 2, pp. 43-50, 2014.

[11] L. F. Tops, N. R. Van de Veire, J. D. Schuijf, A. de Roos, E. E. van der Wall, M. J. Schalij, and J. J. Bax, "Noninvasive evaluation of coronary sinus anatomy and its relation to the mitral valve annulus implications for percutaneous mitral annuloplasty," Circulation, vol. 115, no. 11, pp. 1426-1432, 2007.

[12] A. Plass, I. Valenta, O. Gaemperli, P. Kaufmann, H. Alkadhi, G. Zund, J. Grü-nenfelder, and M. Genoni, "Assessment of coronary sinus anatomy between normal and insufficient mitral valves by multi-slice computer tomography for mitral annuloplasty device implantation," European Journal of Cardio-Thoracic Surgery, vol. 33, no. 4, pp. 583-589, 2008.

[13] A. J. Choure, M. J. Garcia, B. Hesse, M. Sevensma, G. Maly, N. L. Greenberg, L. Borzi, S. Ellis, E. M. Tuzcu, and S. R. Kapadia, "In vivo analysis of the anatomical relationship of coronary sinus to mitral annulus and left circumflex coronary artery using cardiac multidetector computed tomography," Journal of the American College of Cardiology, vol. 48, no. 10, pp. 1938-1945, 2006.

[14] E. Lansac, I. Di Centa, N. Al Attar, D. Messika-Zeitoun, R. Raffoul, A. Vahanian, and P. Nataf, "Percutaneous mitral annuloplasty through the coronary sinus: an anatomic point of view," The Journal of Thoracic and Cardiovascular Surgery, vol. 135, no. 2, pp. 376-381, 2008.

[15] (Accessed Aug. 23, 2017). [Online]. Available: http://www.microlight.fr/static/assets/img/datasheet.pdf

[16] K. Franco and E. Verrier, Advanced Therapy in Cardiac Surgery, ser. Advanced Therapy in Cardiac Surgery. Hamilton, Canada: B. C. Decker, 2003.

[17] M. O. Jensen, H. Jensen, M. Smerup, R. A. Levine, A. P. Yoganathan, H. Nygaard, J. M. Hasenkam, and S. L. Nielsen, "Saddle-shaped mitral valve annuloplasty rings experience lower forces compared with flat rings," Circulation, vol. 118, no. 14, pp. 250-255, 2008.

The invention claimed is:

1. An apparatus for changing a geometry of a mitral valve annulus of a heart, the apparatus comprising:
 an anchor having a body configured to be positioned within and anchored to a coronary sinus vein of the heart, the body having:
  a first end and a second end, the first end being spaced apart from the second end;
  a longitudinally extending axis; and
  a wall with an interior volume extending from the first end to the second end, the interior volume being adapted for receiving a steerable catheter; and
 a first link member having a proximal end nearest to the anchor and a distal end spaced apart from the proximal end, the proximal end of the first link member being coupled to the first end of the anchor by a first joint configured to provide for movement of the first link member in one direction relative to the anchor;
 wherein the distal end of the first link member is movably coupled to the anchor by a first actuating tendon and the proximal end of the first link member is coupled to the anchor by a first release tendon, the first actuating tendon being configured to control the movement of the first link member in a first direction towards the mitral valve annulus to apply a first force to a portion of the mitral valve annulus; and
 wherein the first joint comprises a ratchet having a first pawl and a first plurality of teeth, the first release tendon being coupled to the first pawl to release the first pawl from the first plurality of teeth.

2. The apparatus of claim 1, further comprising a second link member having a proximal end nearest to the anchor and a distal end spaced apart from the proximal end, the proximal end of the second link member being coupled to the distal end of the first link member by a second joint configured to provide for movement of the second link member in one direction relative to the first link member.

3. The apparatus of claim 2, further comprising one or more additional link members, each additional link member having a proximal end nearest the anchor and a distal end spaced apart from the proximal end, the proximal end of each additional link member being coupled to the distal end of an adjacent link member nearer to the anchor by an additional joint configured to provide for movement of the additional link member relative to the adjacent link member in one direction relative to the adjacent link member.

4. The apparatus of claim 2, wherein the distal end of the second link member is movably coupled to the anchor by a second actuating tendon and the proximal end of the second link member is coupled to the anchor by a second release tendon, second actuating tendon being configured to control the movement of the second link member in a second direction towards the mitral valve annulus to apply a second force to a second portion of the mitral valve annulus.

5. The apparatus of claim 4, wherein the second joint comprises a second ratchet having a second pawl and a second plurality of teeth, the second release tendon being coupled to the second pawl to release the second pawl from the second plurality of teeth.

6. The apparatus of claim 1, wherein the first actuating tendon has a first end positioned inside of a first channel of the anchor.

7. The apparatus of claim 6, wherein the first end of the first actuating tendon is sized and shaped to be retained in the first channel.

8. The apparatus of claim 6, wherein the first end of the first actuating tendon is sized and shaped to provide for a grabbing portion of the steerable catheter to grab the first end to actuate the first actuating tendon.

9. The apparatus of claim 4, wherein the first actuating tendon extends through a tendon support of the first link member towards the distal end of the first link member.

10. The apparatus of claim 9, wherein the second actuating tendon extends through the tendon support of the first link member towards the distal end of the second link member.

11. A system for changing a geometry of a mitral valve annulus of a heart, the system comprising:
   an apparatus comprising:
      an anchor having a body configured to be positioned within and anchored to a coronary sinus vein of the heart, the body having:
         a first end and a second end, the first end spaced apart from the second end;
         a longitudinally extending axis; and
         a wall having an interior volume extending from the first end to the second end; and
      a first link member having a proximal end nearest to the anchor and a distal end spaced apart from the proximal end, the proximal end of the first link member being movably coupled to the first end of the anchor by a first joint configured to provide for movement of the first link member in one direction relative to the anchor;
      wherein the distal end of the first link member is movably coupled to the anchor by a first actuating tendon and the proximal end of the first link member is coupled to the anchor by a first release tendon, the first actuating tendon being configured to control the movement of the first link member in a first direction towards the mitral valve annulus to apply a first force to a portion of the mitral valve annulus; and
      wherein the first joint comprises a ratchet having a first pawl and a first plurality of teeth, the first release tendon being coupled to the first pawl to release the first pawl from the first plurality of teeth; and
   a steerable catheter comprising:
      a catheter body; and
      a sub-catheter extending from the catheter body, the sub-catheter being adapted to engage the first link member when the sub-catheter is positioned in the interior volume of the anchor of the apparatus.

12. The system of claim 11, wherein the sub-catheter has a grabbing portion for engaging an actuating tendon of the first link member when the sub-catheter is positioned in the interior volume of the anchor of the apparatus.

13. The system of claim 12, wherein the apparatus comprises additional link members, the grabbing portion of the sub-catheter is configured to engage the additional link members.

14. The system of claim 11, further comprising a second link member having a proximal end nearest to the anchor and a distal end spaced apart from the proximal end, the proximal end of the second link member being movably coupled to the distal end of the first link member by a second joint configured to provide for movement of the second link member in one direction relative to the first link member.

15. The system of claim 11, wherein, upon engaging the first actuating tendon, movement of the sub-catheter controls the movement of the first link member in a direction towards the mitral valve annulus to control a magnitude of the first force applied to a portion of the mitral valve annulus by controlling a position of the first link member with respect to the portion of the mitral valve annulus.

16. The system of claim 11, wherein the anchor further comprises a tendon channel and the sub-catheter engages the first actuating tendon within the tendon channel.

17. The system of claim 16, wherein the anchor further comprises a guiding rail having an opening and the catheter body comprises a guiding channel, the guiding channel being sized and shaped to guide the guiding rail to align the sub-catheter into the tendon channel as the sub-catheter extends into the anchor.

18. A steerable catheter for engaging an apparatus for changing a geometry of a mitral valve annulus of a heart, the apparatus being defined according to claim 1, the steerable catheter comprising:
   a catheter body; and
   a sub-catheter extending from the catheter body, the sub-catheter having a grabbing portion for engaging a tendon of the apparatus when the sub-catheter is inserted into an interior volume of an anchor of the apparatus.

19. The steerable catheter of claim 18, wherein the grabbing portion extends from the sub-catheter to engage a tendon head to engage the tendon.

20. The steerable catheter of claim 19, wherein the grabbing portion is complementary in shape to the tendon head to engage the tendon head.

21. The steerable catheter of claim 18, wherein the steerable catheter further comprises a guiding channel configured to receive a guiding rail of the anchor of the apparatus to align the sub-catheter with the tendon when the sub-catheter is inserted into an interior volume of an anchor of the apparatus.

22. A method of changing a geometry of a mitral valve annulus of a heart, the method comprising:
   implanting an apparatus into a coronary sinus vein of the heart, the apparatus comprising:
      an anchor having a body, the body having:
         a first end and a second end, the first end spaced apart from the second end;
         a longitudinally extending axis;
         a wall having an interior volume extending from the first end to the second end; and
         a first link member having a proximal end nearest to the anchor and a distal end spaced apart from the proximal end, the proximal end of the first link member being movably coupled to the first end of the anchor by a first joint configured to provide for movement of the first link member in one direction relative to the anchor;

wherein the distal end of the first link member is movably coupled to the anchor by a first actuating tendon and the proximal end of the first link member is coupled to the anchor by a first release tendon, the first actuating tendon being configured to control the movement of the first link member in a first direction towards the mitral valve annulus to apply a first force to a portion of the mitral valve annulus; and wherein the first joint comprises a ratchet having a first pawl and a first plurality of teeth, the first release tendon being coupled to the first pawl to release the first pawl from the first plurality of teeth; and adjusting the apparatus with a steerable catheter, the steerable catheter comprising:

a catheter body; and a sub-catheter extending from the catheter body, the sub-catheter engaging the apparatus when the sub-catheter is inserted into the interior volume of the anchor to adjust a position of the first link member to apply a force against the mitral valve to change the geometry of the mitral valve annulus.

23. The method of claim 22, wherein the sub-catheter has a grabbing portion to engage the first link member when the sub-catheter is inserted into the interior volume of the anchor.

24. The method of claim 23, wherein when the apparatus comprises additional link members, the grabbing portion of the sub-catheter is configured to engage the additional link members.

25. The method of claim 22, wherein the adjustment of the apparatus occurs: (a) immediately after implantation of the apparatus, (b) during a same surgical procedure as the implanting the apparatus or (c) during a subsequent surgical procedure after the procedure for implanting the apparatus.

* * * * *